(12) United States Patent
Crowley et al.

(10) Patent No.: US 10,342,660 B2
(45) Date of Patent: Jul. 9, 2019

(54) TENSIONED SHEATHING AIDS

(71) Applicant: BOSTON SCIENTIFIC SCIMED, INC., Maple Grove, MN (US)

(72) Inventors: Cornelius M. Crowley, San Francisco, CA (US); Ali Salahieh, Saratoga, CA (US); Brian D. Brandt, Morgan Hill, CA (US); Andrew J. H. Backus, Santa Cruz, CA (US); Thu Pham, San Jose, CA (US); Luan Cao, Stockton, CA (US); Dwight J. Knab, Jr., Newark, CA (US)

(73) Assignee: BOSTON SCIENTIFIC INC., Maple Grove, MN (US)

( * ) Notice: Subject to any disclaimer, the term of this patent is extended or adjusted under 35 U.S.C. 154(b) by 209 days.

(21) Appl. No.: 15/413,642

(22) Filed: Jan. 24, 2017

(65) Prior Publication Data

US 2017/0216029 A1    Aug. 3, 2017

Related U.S. Application Data

(60) Provisional application No. 62/289,993, filed on Feb. 2, 2016.

(51) Int. Cl.
*A61F 2/95* (2013.01)
*A61F 2/24* (2006.01)
*A61F 2/966* (2013.01)

(52) U.S. Cl.
CPC .......... *A61F 2/2436* (2013.01); *A61F 2/2418* (2013.01); *A61F 2/2439* (2013.01);
(Continued)

(58) Field of Classification Search
CPC ................. A61F 2/95–97; A61F 2/2427–2439
See application file for complete search history.

(56) References Cited

U.S. PATENT DOCUMENTS

| 15,192 A | 6/1856 | Peale |
| 2,682,057 A | 6/1954 | Lord |
(Continued)

FOREIGN PATENT DOCUMENTS

| CN | 1338951 A | 3/2002 |
| DE | 19532846 A1 | 3/1997 |
(Continued)

OTHER PUBLICATIONS

Andersen et al., "Transluminal implantation of artificial heart valves. Description of a new expandable aortic valve and initial results with implantation by catheter technique in closed chest pigs." Euro. Heart J., 13:704-708, May 1992.
(Continued)

*Primary Examiner* — Kathleen S Holwerda
(74) *Attorney, Agent, or Firm* — Seager, Tufte & Wickhem LLP

(57) ABSTRACT

A medical device apparatus may include a medical implant including an anchor member configured to actuate between a delivery configuration and a deployed configuration operatively connected to a delivery system, the delivery system including an outer sheath and an inner catheter disposed within the outer sheath, and a sheathing aid connecting the delivery system to the medical implant, the sheathing aid being configured to guide the medical implant into the outer sheath upon relative closing movement therebetween. The sheathing aid may include a plurality of tethers extending from the inner catheter to a proximal end of the anchor member, and a release mechanism slidably disposed within a coupler ring coupled to a distal end of the inner catheter. The plurality of tethers may be releasably coupled to the release mechanism.

16 Claims, 20 Drawing Sheets

(52) U.S. Cl.
CPC .............. *A61F 2002/9511* (2013.01); *A61F 2002/9534* (2013.01); *A61F 2002/9665* (2013.01)

(56) References Cited

U.S. PATENT DOCUMENTS

| | | |
|---|---|---|
| 2,701,559 A | 2/1955 | Cooper |
| 2,832,078 A | 4/1958 | Williams |
| 3,099,016 A | 7/1963 | Edwards |
| 3,113,586 A | 12/1963 | Edmark, Jr. |
| 3,130,418 A | 4/1964 | Head et al. |
| 3,143,742 A | 8/1964 | Cromie |
| 3,334,629 A | 5/1967 | Cohn |
| 3,367,364 A | 2/1968 | Cruz, Jr. et al. |
| 3,409,013 A | 11/1968 | Berry |
| 3,445,916 A | 5/1969 | Schulte |
| 3,540,431 A | 11/1970 | Mobin-Uddin |
| 3,548,417 A | 12/1970 | Kischer et al. |
| 3,570,014 A | 3/1971 | Hancock |
| 3,587,115 A | 6/1971 | Shiley |
| 3,592,184 A | 7/1971 | Watkins et al. |
| 3,628,535 A | 12/1971 | Ostrowsky et al. |
| 3,642,004 A | 2/1972 | Osthagen et al. |
| 3,657,744 A | 4/1972 | Ersek |
| 3,671,979 A | 6/1972 | Moulopoulos |
| 3,714,671 A | 2/1973 | Edwards et al. |
| 3,755,823 A | 9/1973 | Hancock |
| 3,795,246 A | 3/1974 | Sturgeon |
| 3,839,741 A | 10/1974 | Haller |
| 3,868,956 A | 3/1975 | Alfidi et al. |
| 3,874,388 A | 4/1975 | King et al. |
| 3,997,923 A | 12/1976 | Possis |
| 4,035,849 A | 7/1977 | Angell et al. |
| 4,056,854 A | 11/1977 | Boretos et al. |
| 4,106,129 A | 8/1978 | Carpentier et al. |
| 4,222,126 A | 9/1980 | Boretos et al. |
| 4,233,690 A | 11/1980 | Akins |
| 4,265,694 A | 5/1981 | Boretos et al. |
| 4,291,420 A | 9/1981 | Reul |
| 4,297,749 A | 11/1981 | Davis et al. |
| 4,323,358 A | 4/1982 | Lentz et al. |
| 4,326,306 A | 4/1982 | Poler |
| 4,339,831 A | 7/1982 | Johnson |
| 4,343,048 A | 8/1982 | Ross et al. |
| 4,345,340 A | 8/1982 | Rosen |
| 4,373,216 A | 2/1983 | Klawitter |
| 4,406,022 A | 9/1983 | Roy |
| 4,423,809 A | 1/1984 | Mazzocco |
| 4,425,908 A | 1/1984 | Simon |
| 4,470,157 A | 9/1984 | Love |
| 4,484,579 A | 11/1984 | Meno et al. |
| 4,501,030 A | 2/1985 | Lane |
| 4,531,943 A | 7/1985 | Van Tassel et al. |
| 4,535,483 A | 8/1985 | Klawitter et al. |
| 4,574,803 A | 3/1986 | Storz |
| 4,580,568 A | 4/1986 | Gianturco |
| 4,592,340 A | 6/1986 | Boyles |
| 4,602,911 A | 7/1986 | Ahmadi et al. |
| 4,605,407 A | 8/1986 | Black et al. |
| 4,610,688 A | 9/1986 | Silvestrini et al. |
| 4,612,011 A | 9/1986 | Kautzky |
| 4,617,932 A | 10/1986 | Kornberg |
| 4,643,732 A | 2/1987 | Pietsch et al. |
| 4,647,283 A | 3/1987 | Carpentier et al. |
| 4,648,881 A | 3/1987 | Carpentier et al. |
| 4,655,218 A | 4/1987 | Kulik et al. |
| 4,655,771 A | 4/1987 | Wallsten |
| 4,662,885 A | 5/1987 | Dipisa, Jr. |
| 4,665,906 A | 5/1987 | Jervis |
| 4,680,031 A | 7/1987 | Alonso |
| 4,692,164 A | 9/1987 | Dzemeshkevich et al. |
| 4,705,516 A | 11/1987 | Barone et al. |
| 4,710,192 A | 12/1987 | Liotta et al. |
| 4,733,665 A | 3/1988 | Palmaz |
| 4,755,181 A | 7/1988 | Igoe |
| 4,759,758 A | 7/1988 | Gabbay |
| 4,777,951 A | 10/1988 | Cribier et al. |
| 4,787,899 A | 11/1988 | Lazarus |
| 4,787,901 A | 11/1988 | Baykut |
| 4,796,629 A | 1/1989 | Grayzel |
| 4,819,751 A | 4/1989 | Shimada et al. |
| 4,829,990 A | 5/1989 | Thuroff et al. |
| 4,834,755 A | 5/1989 | Silvestrini et al. |
| 4,851,001 A | 7/1989 | Taheri |
| 4,856,516 A | 8/1989 | Hillstead |
| 4,865,600 A | 9/1989 | Carpentier et al. |
| 4,872,874 A | 10/1989 | Taheri |
| 4,873,978 A | 10/1989 | Ginsburg |
| 4,878,495 A | 11/1989 | Grayzel |
| 4,878,906 A | 11/1989 | Lindemann et al. |
| 4,883,458 A | 11/1989 | Shiber |
| 4,885,005 A | 12/1989 | Nashef et al. |
| 4,909,252 A | 3/1990 | Goldberger |
| 4,917,102 A | 4/1990 | Miller et al. |
| 4,922,905 A | 5/1990 | Strecker |
| 4,927,426 A | 5/1990 | Dretler |
| 4,954,126 A | 9/1990 | Wallsten |
| 4,966,604 A | 10/1990 | Reiss |
| 4,969,890 A | 11/1990 | Sugita et al. |
| 4,979,939 A | 12/1990 | Shiber |
| 4,986,830 A | 1/1991 | Owens et al. |
| 4,994,077 A | 2/1991 | Dobben |
| 5,002,556 A | 3/1991 | Ishida et al. |
| 5,002,559 A | 3/1991 | Tower |
| 5,007,896 A | 4/1991 | Shiber |
| 5,026,366 A | 6/1991 | Leckrone |
| 5,032,128 A | 7/1991 | Alonso |
| 5,037,434 A | 8/1991 | Lane |
| 5,047,041 A | 9/1991 | Samuels |
| 5,064,435 A | 11/1991 | Porter |
| 5,080,668 A | 1/1992 | Bolz et al. |
| 5,085,635 A | 2/1992 | Cragg |
| 5,089,015 A | 2/1992 | Ross |
| 5,132,473 A | 7/1992 | Furutaka et al. |
| 5,141,494 A | 8/1992 | Danforth et al. |
| 5,152,771 A | 10/1992 | Sabbaghian et al. |
| 5,159,937 A | 11/1992 | Tremulis |
| 5,161,547 A | 11/1992 | Tower |
| 5,163,953 A | 11/1992 | Vince |
| 5,167,628 A | 12/1992 | Boyles |
| 5,209,741 A | 5/1993 | Spaeth |
| 5,215,541 A | 6/1993 | Nashef et al. |
| 5,217,483 A | 6/1993 | Tower |
| 5,238,004 A | 8/1993 | Sahatjian et al. |
| 5,258,023 A | 11/1993 | Reger |
| 5,258,042 A | 11/1993 | Mehta |
| 5,282,847 A | 2/1994 | Trescony et al. |
| 5,295,958 A | 3/1994 | Shturman |
| 5,332,402 A | 7/1994 | Teitelbaum |
| 5,336,258 A | 8/1994 | Quintero et al. |
| 5,350,398 A | 9/1994 | Pavcnik et al. |
| 5,360,444 A | 11/1994 | Kusuhara |
| 5,370,685 A | 12/1994 | Stevens |
| 5,387,235 A * | 2/1995 | Chuter ............... A61B 17/0469 606/194 |
| 5,389,106 A | 2/1995 | Tower |
| 5,397,351 A | 3/1995 | Pavcnik et al. |
| 5,409,019 A | 4/1995 | Wilk |
| 5,411,552 A | 5/1995 | Andersen et al. |
| 5,425,762 A | 6/1995 | Muller |
| 5,431,676 A | 7/1995 | Dubrul et al. |
| 5,443,446 A | 8/1995 | Shturman |
| 5,443,449 A | 8/1995 | Buelna |
| 5,443,477 A | 8/1995 | Mann et al. |
| 5,443,495 A | 8/1995 | Buscemi et al. |
| 5,443,499 A | 8/1995 | Schmitt |
| 5,476,506 A | 12/1995 | Lunn |
| 5,476,510 A | 12/1995 | Eberhardt et al. |
| 5,480,423 A | 1/1996 | Ravenscroft et al. |
| 5,480,424 A | 1/1996 | Cox |
| 5,500,014 A | 3/1996 | Quijano et al. |
| 5,507,767 A | 4/1996 | Maeda et al. |
| 5,534,007 A | 7/1996 | St. Germain et al. |
| 5,545,133 A | 8/1996 | Burns et al. |

(56) References Cited

U.S. PATENT DOCUMENTS

| | | |
|---|---|---|
| 5,545,209 A | 8/1996 | Roberts et al. |
| 5,545,211 A | 8/1996 | An et al. |
| 5,545,214 A | 8/1996 | Stevens |
| 5,549,665 A | 8/1996 | Vesely et al. |
| 5,554,185 A | 9/1996 | Block et al. |
| 5,571,175 A | 11/1996 | Vanney et al. |
| 5,571,215 A | 11/1996 | Sterman et al. |
| 5,573,520 A | 11/1996 | Schwartz et al. |
| 5,575,818 A | 11/1996 | Pinchuk |
| 5,591,185 A | 1/1997 | Kilmer et al. |
| 5,591,195 A | 1/1997 | Taheri et al. |
| 5,607,464 A | 3/1997 | Trescony et al. |
| 5,609,626 A | 3/1997 | Quijano et al. |
| 5,645,559 A | 7/1997 | Hachtman et al. |
| 5,662,671 A | 9/1997 | Barbut et al. |
| 5,667,523 A | 9/1997 | Bynon et al. |
| 5,674,277 A | 10/1997 | Freitag |
| 5,693,083 A | 12/1997 | Baker et al. |
| 5,693,310 A | 12/1997 | Gries et al. |
| 5,695,498 A | 12/1997 | Tower |
| 5,709,713 A | 1/1998 | Evans et al. |
| 5,713,951 A | 2/1998 | Garrison et al. |
| 5,713,953 A | 2/1998 | Vallana et al. |
| 5,716,370 A | 2/1998 | Williamson, IV et al. |
| 5,716,417 A | 2/1998 | Girard et al. |
| 5,720,391 A | 2/1998 | Dohm et al. |
| 5,725,549 A | 3/1998 | Lam |
| 5,728,068 A | 3/1998 | Leone et al. |
| 5,733,325 A | 3/1998 | Robinson et al. |
| 5,735,842 A | 4/1998 | Krueger et al. |
| 5,749,890 A | 5/1998 | Shaknovich |
| 5,755,783 A | 5/1998 | Stobie et al. |
| 5,756,476 A | 5/1998 | Epstein et al. |
| 5,769,812 A | 6/1998 | Stevens et al. |
| 5,772,609 A | 6/1998 | Nguyen et al. |
| 5,800,456 A | 9/1998 | Maeda et al. |
| 5,800,531 A | 9/1998 | Cosgrove et al. |
| 5,807,405 A | 9/1998 | Vanney et al. |
| 5,817,126 A | 10/1998 | Imran |
| 5,824,041 A | 10/1998 | Lenker et al. |
| 5,824,043 A | 10/1998 | Cottone, Jr. |
| 5,824,053 A | 10/1998 | Khosravi et al. |
| 5,824,055 A | 10/1998 | Spiridigliozzi et al. |
| 5,824,056 A | 10/1998 | Rosenberg |
| 5,824,064 A | 10/1998 | Taheri |
| 5,840,081 A | 11/1998 | Andersen et al. |
| 5,843,158 A | 12/1998 | Lenker et al. |
| 5,855,597 A | 1/1999 | Jayaraman |
| 5,855,601 A | 1/1999 | Bessler et al. |
| 5,855,602 A | 1/1999 | Angell |
| 5,860,966 A | 1/1999 | Tower |
| 5,861,024 A | 1/1999 | Rashidi |
| 5,861,028 A | 1/1999 | Angell |
| 5,868,783 A | 2/1999 | Tower |
| 5,876,419 A | 3/1999 | Carpenter et al. |
| 5,876,448 A | 3/1999 | Thompson et al. |
| 5,885,228 A | 3/1999 | Rosenman et al. |
| 5,888,201 A | 3/1999 | Stinson et al. |
| 5,891,191 A | 4/1999 | Stinson |
| 5,895,399 A | 4/1999 | Barbut et al. |
| 5,906,619 A | 5/1999 | Olson et al. |
| 5,907,893 A | 6/1999 | Ladno-Azizi et al. |
| 5,910,154 A | 6/1999 | Tsugita et al. |
| 5,911,734 A | 6/1999 | Tsugita et al. |
| 5,925,063 A | 7/1999 | Khosravi |
| 5,944,738 A | 8/1999 | Amplatz et al. |
| 5,954,766 A | 9/1999 | Ladno-Azizi et al. |
| 5,957,949 A | 9/1999 | Leonhardt et al. |
| 5,968,070 A | 10/1999 | Bley et al. |
| 5,984,957 A | 11/1999 | Laptewicz, Jr. et al. |
| 5,984,959 A | 11/1999 | Robertson et al. |
| 5,993,469 A | 11/1999 | McKenzie et al. |
| 5,997,557 A | 12/1999 | Barbut et al. |
| 6,010,522 A | 1/2000 | Barbut et al. |
| 6,022,370 A | 2/2000 | Tower |
| 6,027,520 A | 2/2000 | Tsugita et al. |
| 6,027,525 A | 2/2000 | Suh et al. |
| 6,042,598 A | 3/2000 | Tsugita et al. |
| 6,042,607 A | 3/2000 | Williamson, IV et al. |
| 6,051,014 A | 4/2000 | Jang |
| 6,059,827 A | 5/2000 | Fenton, Jr. |
| 6,074,418 A | 6/2000 | Buchanan et al. |
| 6,093,203 A | 7/2000 | Uflacker |
| 6,096,074 A | 8/2000 | Pedros |
| 6,123,723 A | 9/2000 | Konya et al. |
| 6,132,473 A | 10/2000 | Williams et al. |
| 6,139,510 A | 10/2000 | Palermo |
| 6,142,987 A | 11/2000 | Tsugita |
| 6,146,366 A | 11/2000 | Schachar |
| 6,162,245 A | 12/2000 | Jayaraman |
| 6,165,200 A | 12/2000 | Tsugita et al. |
| 6,165,209 A | 12/2000 | Patterson et al. |
| 6,168,579 B1 | 1/2001 | Tsugita |
| 6,168,614 B1 | 1/2001 | Andersen et al. |
| 6,171,327 B1 | 1/2001 | Daniel et al. |
| 6,171,335 B1 | 1/2001 | Wheatley et al. |
| 6,179,859 B1 | 1/2001 | Bates et al. |
| 6,187,016 B1 | 2/2001 | Hedges et al. |
| 6,197,053 B1 | 3/2001 | Cosgrove et al. |
| 6,200,336 B1 | 3/2001 | Pavcnik et al. |
| 6,214,036 B1 | 4/2001 | Letendre et al. |
| 6,221,006 B1 | 4/2001 | Dubrul et al. |
| 6,221,091 B1 | 4/2001 | Khosravi |
| 6,221,096 B1 | 4/2001 | Aiba et al. |
| 6,221,100 B1 | 4/2001 | Strecker |
| 6,231,544 B1 | 5/2001 | Tsuigita et al. |
| 6,231,551 B1 | 5/2001 | Barbut |
| 6,241,757 B1 | 6/2001 | An et al. |
| 6,245,102 B1 | 6/2001 | Jayaraman |
| 6,251,135 B1 | 6/2001 | Stinson et al. |
| 6,258,114 B1 | 7/2001 | Konya et al. |
| 6,258,115 B1 | 7/2001 | Dubrul |
| 6,258,120 B1 | 7/2001 | McKenzie et al. |
| 6,258,129 B1 | 7/2001 | Dybdal et al. |
| 6,267,783 B1 | 7/2001 | Letendre et al. |
| 6,270,513 B1 | 8/2001 | Tsugita et al. |
| 6,277,555 B1 | 8/2001 | Duran et al. |
| 6,299,637 B1 | 10/2001 | Shaolian et al. |
| 6,302,906 B1 | 10/2001 | Goicoechea et al. |
| 6,309,417 B1 | 10/2001 | Spence et al. |
| 6,319,281 B1 | 11/2001 | Patel |
| 6,327,772 B1 | 12/2001 | Zadno-Azizi et al. |
| 6,336,934 B1 | 1/2002 | Gilson et al. |
| 6,336,937 B1 | 1/2002 | Vonesh et al. |
| 6,338,735 B1 | 1/2002 | Stevens |
| 6,346,116 B1 | 2/2002 | Brooks et al. |
| 6,348,063 B1 | 2/2002 | Yassour et al. |
| 6,352,554 B2 | 3/2002 | De Paulis |
| 6,352,708 B1 | 3/2002 | Duran et al. |
| 6,361,545 B1 | 3/2002 | Macoviak et al. |
| 6,363,938 B2 | 4/2002 | Saadat et al. |
| 6,364,895 B1 | 4/2002 | Greenhalgh |
| 6,371,970 B1 | 4/2002 | Khosravi et al. |
| 6,371,983 B1 | 4/2002 | Lane |
| 6,379,383 B1 | 4/2002 | Palmaz et al. |
| 6,398,807 B1 | 6/2002 | Chouinard et al. |
| 6,402,736 B1 | 6/2002 | Brown et al. |
| 6,409,750 B1 | 6/2002 | Hyodoh et al. |
| 6,416,510 B1 | 7/2002 | Altman et al. |
| 6,425,916 B1 | 7/2002 | Garrison et al. |
| 6,440,164 B1 | 8/2002 | DiMatteo et al. |
| 6,454,799 B1 | 9/2002 | Schreck |
| 6,458,153 B1 | 10/2002 | Bailey et al. |
| 6,461,382 B1 | 10/2002 | Cao |
| 6,468,303 B1 | 10/2002 | Amplatz et al. |
| 6,468,660 B2 | 10/2002 | Ogle et al. |
| 6,475,239 B1 | 11/2002 | Campbell et al. |
| 6,482,228 B1 | 11/2002 | Norred |
| 6,485,501 B1 | 11/2002 | Green |
| 6,485,502 B2 | 11/2002 | Don Michael et al. |
| 6,488,704 B1 | 12/2002 | Connelly et al. |
| 6,494,909 B2 | 12/2002 | Greenhalgh |
| 6,503,272 B2 | 1/2003 | Duerig et al. |
| 6,508,803 B1 | 1/2003 | Horikawa et al. |

(56) References Cited

U.S. PATENT DOCUMENTS

| | | |
|---|---|---|
| 6,508,833 B2 | 1/2003 | Pavcnik et al. |
| 6,527,800 B1 | 3/2003 | McGuckin, Jr. et al. |
| 6,530,949 B2 | 3/2003 | Konya et al. |
| 6,530,952 B2 | 3/2003 | Vesely |
| 6,537,297 B2 | 3/2003 | Tsugita et al. |
| 6,540,768 B1 | 4/2003 | Diaz et al. |
| 6,562,058 B2 | 5/2003 | Seguin et al. |
| 6,569,196 B1 | 5/2003 | Vesely |
| 6,572,643 B1 | 6/2003 | Gharibadeh |
| 6,585,766 B1 | 7/2003 | Huynh et al. |
| 6,592,546 B1 | 7/2003 | Barbut et al. |
| 6,592,614 B2 | 7/2003 | Lenker et al. |
| 6,605,112 B1 | 8/2003 | Moll et al. |
| 6,610,077 B1 | 8/2003 | Hancock et al. |
| 6,616,682 B2 | 9/2003 | Joergensen et al. |
| 6,622,604 B1 | 9/2003 | Chouinard et al. |
| 6,623,518 B2 | 9/2003 | Thompson et al. |
| 6,623,521 B2 | 9/2003 | Steinke et al. |
| 6,632,243 B1 | 10/2003 | Zadno-Azizi et al. |
| 6,635,068 B1 | 10/2003 | Dubrul et al. |
| 6,635,079 B2 | 10/2003 | Unsworth et al. |
| 6,652,571 B1 | 11/2003 | White et al. |
| 6,652,578 B2 | 11/2003 | Bailey et al. |
| 6,663,588 B2 | 12/2003 | DuBois et al. |
| 6,663,663 B2 | 12/2003 | Kim et al. |
| 6,669,724 B2 | 12/2003 | Park et al. |
| 6,673,089 B1 | 1/2004 | Yassour et al. |
| 6,673,109 B2 | 1/2004 | Cox |
| 6,676,668 B2 | 1/2004 | Mercereau et al. |
| 6,676,692 B2 | 1/2004 | Rabkin et al. |
| 6,676,698 B2 | 1/2004 | McGuckin, Jr. et al. |
| 6,682,543 B2 | 1/2004 | Barbut et al. |
| 6,682,558 B2 | 1/2004 | Tu et al. |
| 6,682,559 B2 | 1/2004 | Myers et al. |
| 6,685,739 B2 | 2/2004 | DiMatteo et al. |
| 6,689,144 B2 | 2/2004 | Gerberding |
| 6,689,164 B1 | 2/2004 | Seguin |
| 6,692,512 B2 | 2/2004 | Jang |
| 6,695,864 B2 | 2/2004 | Macoviak et al. |
| 6,695,865 B2 | 2/2004 | Boyle et al. |
| 6,702,851 B1 | 3/2004 | Chinn et al. |
| 6,712,842 B1 | 3/2004 | Gifford, III et al. |
| 6,712,843 B2 | 3/2004 | Elliott |
| 6,714,842 B1 | 3/2004 | Ito |
| 6,719,789 B2 | 4/2004 | Cox |
| 6,723,116 B2 | 4/2004 | Taheri |
| 6,730,118 B2 | 5/2004 | Spenser et al. |
| 6,730,377 B2 | 5/2004 | Wang |
| 6,733,525 B2 | 5/2004 | Yang et al. |
| 6,736,846 B2 | 5/2004 | Cox |
| 6,752,828 B2 | 6/2004 | Thornton |
| 6,755,854 B2 | 6/2004 | Gillick et al. |
| 6,758,855 B2 | 7/2004 | Fulton, III et al. |
| 6,764,503 B1 | 7/2004 | Ishimaru |
| 6,764,509 B2 | 7/2004 | Chinn et al. |
| 6,767,345 B2 | 7/2004 | St. Germain et al. |
| 6,769,434 B2 | 8/2004 | Liddicoat et al. |
| 6,773,454 B2 | 8/2004 | Wholey et al. |
| 6,776,791 B1 | 8/2004 | Stallings et al. |
| 6,786,925 B1 | 9/2004 | Schoon et al. |
| 6,790,229 B1 | 9/2004 | Berreklouw |
| 6,790,230 B2 | 9/2004 | Beyersdorf et al. |
| 6,790,237 B2 | 9/2004 | Stinson |
| 6,792,979 B2 | 9/2004 | Konya et al. |
| 6,797,002 B2 | 9/2004 | Spence et al. |
| 6,814,746 B2 | 11/2004 | Thompson et al. |
| 6,821,297 B2 | 11/2004 | Snyders |
| 6,830,585 B1 | 12/2004 | Artof et al. |
| 6,837,901 B2 | 1/2005 | Rabkin et al. |
| 6,840,957 B2 | 1/2005 | DiMatteo et al. |
| 6,843,802 B1 | 1/2005 | Villalobos et al. |
| 6,849,085 B2 | 2/2005 | Marton |
| 6,863,668 B2 | 3/2005 | Gillespie et al. |
| 6,866,650 B2 | 3/2005 | Stevens et al. |
| 6,866,669 B2 | 3/2005 | Buzzard et al. |
| 6,872,223 B2 | 3/2005 | Roberts et al. |
| 6,872,226 B2 | 3/2005 | Cali et al. |
| 6,875,231 B2 | 4/2005 | Anduiza et al. |
| 6,881,220 B2 | 4/2005 | Edwin et al. |
| 6,887,266 B2 | 5/2005 | Williams et al. |
| 6,890,340 B2 | 5/2005 | Duane |
| 6,893,459 B1 | 5/2005 | Macoviak |
| 6,893,460 B2 | 5/2005 | Spenser et al. |
| 6,905,743 B1 | 6/2005 | Chen et al. |
| 6,908,481 B2 | 6/2005 | Cribier |
| 6,911,036 B2 | 6/2005 | Douk et al. |
| 6,911,043 B2 | 6/2005 | Myers et al. |
| 6,936,058 B2 | 8/2005 | Forde et al. |
| 6,936,067 B2 | 8/2005 | Buchanan |
| 6,939,352 B2 | 9/2005 | Buzzard et al. |
| 6,951,571 B1 | 10/2005 | Srivastava |
| 6,953,332 B1 | 10/2005 | Kurk et al. |
| 6,964,673 B2 | 11/2005 | Tsugita et al. |
| 6,969,395 B2 | 11/2005 | Eskuri |
| 6,972,025 B2 | 12/2005 | WasDyke |
| 6,974,464 B2 | 12/2005 | Quijano et al. |
| 6,974,474 B2 | 12/2005 | Pavcnik et al. |
| 6,974,476 B2 | 12/2005 | McGuckin, Jr. et al. |
| 6,979,350 B2 | 12/2005 | Moll et al. |
| 6,984,242 B2 | 1/2006 | Campbell et al. |
| 6,989,027 B2 | 1/2006 | Allen et al. |
| 7,004,176 B2 | 2/2006 | Lau |
| 7,011,681 B2 | 3/2006 | Vesely |
| 7,018,406 B2 | 3/2006 | Seguin et al. |
| 7,025,791 B2 | 4/2006 | Levine et al. |
| 7,037,331 B2 | 5/2006 | Mitelberg et al. |
| 7,041,132 B2 | 5/2006 | Quijano et al. |
| 7,097,658 B2 | 8/2006 | Oktay |
| 7,122,020 B2 | 10/2006 | Mogul |
| 7,125,418 B2 | 10/2006 | Duran et al. |
| 7,141,063 B2 | 11/2006 | White et al. |
| 7,166,097 B2 | 1/2007 | Barbut |
| 7,175,653 B2 | 2/2007 | Gaber |
| 7,175,654 B2 | 2/2007 | Bonsignore et al. |
| 7,175,656 B2 | 2/2007 | Khairkhahan |
| 7,189,258 B2 | 3/2007 | Johnson et al. |
| 7,191,018 B2 | 3/2007 | Gielen et al. |
| 7,201,772 B2 | 4/2007 | Schwammenthal et al. |
| 7,235,093 B2 | 6/2007 | Gregorich |
| 7,258,696 B2 | 8/2007 | Rabkin et al. |
| 7,267,686 B2 | 9/2007 | DiMatteo et al. |
| 7,276,078 B2 | 10/2007 | Spenser et al. |
| 7,322,932 B2 | 1/2008 | Xie et al. |
| 7,326,236 B2 | 2/2008 | Andreas et al. |
| 7,329,279 B2 | 2/2008 | Haug et al. |
| 7,374,560 B2 | 5/2008 | Ressemann et al. |
| 7,381,219 B2 | 6/2008 | Salahieh et al. |
| 7,381,220 B2 | 6/2008 | Macoviak et al. |
| 7,399,315 B2 | 7/2008 | Iobbi |
| 7,445,631 B2 | 11/2008 | Salahieh et al. |
| 7,470,285 B2 | 12/2008 | Nugent et al. |
| 7,491,232 B2 | 2/2009 | Bolduc et al. |
| 7,510,574 B2 | 3/2009 | Lê et al. |
| 7,524,330 B2 | 4/2009 | Berreklouw |
| 7,530,995 B2 | 5/2009 | Quijano et al. |
| 7,544,206 B2 | 6/2009 | Cohn |
| 7,622,276 B2 | 11/2009 | Cunanan et al. |
| 7,628,803 B2 | 12/2009 | Pavcnik et al. |
| 7,632,298 B2 | 12/2009 | Hijlkema et al. |
| 7,674,282 B2 | 3/2010 | Wu et al. |
| 7,712,606 B2 | 5/2010 | Salahieh et al. |
| 7,722,638 B2 | 5/2010 | Deyette, Jr. et al. |
| 7,722,662 B2 | 5/2010 | Steinke et al. |
| 7,722,666 B2 | 5/2010 | Lafontaine |
| 7,736,388 B2 | 6/2010 | Goldfarb et al. |
| 7,748,389 B2 | 7/2010 | Salahieh et al. |
| 7,758,625 B2 | 7/2010 | Wu et al. |
| 7,780,725 B2 | 8/2010 | Haug et al. |
| 7,799,065 B2 | 9/2010 | Pappas |
| 7,803,185 B2 | 9/2010 | Gabbay |
| 7,824,442 B2 | 11/2010 | Salahieh et al. |
| 7,824,443 B2 | 11/2010 | Salahieh et al. |
| 7,833,262 B2 | 11/2010 | McGuckin, Jr. et al. |
| 7,846,204 B2 | 12/2010 | Letac et al. |

(56) References Cited

U.S. PATENT DOCUMENTS

| | | |
|---|---|---|
| 7,892,292 B2 | 2/2011 | Stack et al. |
| 7,918,880 B2 | 4/2011 | Austin |
| 7,938,851 B2 | 5/2011 | Olson et al. |
| 7,959,666 B2 | 6/2011 | Salahieh et al. |
| 7,959,672 B2 | 6/2011 | Salahieh et al. |
| 7,988,724 B2 | 8/2011 | Salahieh et al. |
| 8,048,153 B2 | 11/2011 | Salahieh et al. |
| 8,052,749 B2 | 11/2011 | Salahieh et al. |
| 8,136,659 B2 | 3/2012 | Salahieh et al. |
| 8,157,853 B2 | 4/2012 | Laske et al. |
| 8,182,528 B2 | 5/2012 | Salahieh et al. |
| 8,192,351 B2 | 6/2012 | Fishler et al. |
| 8,226,710 B2 | 7/2012 | Nguyen et al. |
| 8,231,670 B2 | 7/2012 | Salahieh et al. |
| 8,236,049 B2 | 8/2012 | Rowe et al. |
| 8,246,678 B2 | 8/2012 | Salahieh et al. |
| 8,252,051 B2 | 8/2012 | Chau et al. |
| 8,252,052 B2 | 8/2012 | Salahieh et al. |
| 8,287,584 B2 | 10/2012 | Salahieh et al. |
| 8,308,798 B2 | 11/2012 | Pintor et al. |
| 8,323,335 B2 | 12/2012 | Rowe et al. |
| 8,328,868 B2 | 12/2012 | Paul et al. |
| 8,343,213 B2 | 1/2013 | Salahieh et al. |
| 8,376,865 B2 | 2/2013 | Forster et al. |
| 8,377,117 B2 | 2/2013 | Keidar et al. |
| 8,398,708 B2 | 3/2013 | Meiri et al. |
| 8,579,962 B2 | 11/2013 | Salahieh et al. |
| 8,603,160 B2 | 12/2013 | Salahieh et al. |
| 8,617,236 B2 | 12/2013 | Paul et al. |
| 8,623,074 B2 | 1/2014 | Ryan |
| 8,623,076 B2 | 1/2014 | Salahieh et al. |
| 8,623,078 B2 | 1/2014 | Salahieh et al. |
| 8,668,733 B2 | 3/2014 | Haug et al. |
| 8,828,078 B2 | 9/2014 | Salahieh et al. |
| 8,840,662 B2 | 9/2014 | Salahieh et al. |
| 8,840,663 B2 | 9/2014 | Salahieh et al. |
| 8,858,620 B2 | 10/2014 | Salahieh et al. |
| 2001/0002445 A1 | 5/2001 | Vesely |
| 2001/0007956 A1 | 7/2001 | Letac et al. |
| 2001/0010017 A1 | 7/2001 | Letac et al. |
| 2001/0021872 A1 | 9/2001 | Bailey et al. |
| 2001/0025196 A1 | 9/2001 | Chinn et al. |
| 2001/0032013 A1 | 10/2001 | Marton |
| 2001/0039450 A1 | 11/2001 | Pavcnik et al. |
| 2001/0041928 A1 | 11/2001 | Pavcnik et al. |
| 2001/0041930 A1 | 11/2001 | Globerman et al. |
| 2001/0044634 A1 | 11/2001 | Don Michael et al. |
| 2001/0044652 A1 | 11/2001 | Moore |
| 2001/0044656 A1 | 11/2001 | Williamson, IV et al. |
| 2002/0002396 A1 | 1/2002 | Fulkerson |
| 2002/0010489 A1 | 1/2002 | Grayzel et al. |
| 2002/0026233 A1 | 2/2002 | Shaknovich |
| 2002/0029014 A1 | 3/2002 | Jayaraman |
| 2002/0029981 A1 | 3/2002 | Nigam |
| 2002/0032480 A1 | 3/2002 | Spence et al. |
| 2002/0032481 A1 | 3/2002 | Gabbay |
| 2002/0042651 A1 | 4/2002 | Liddicoat et al. |
| 2002/0052651 A1 | 5/2002 | Myers et al. |
| 2002/0055767 A1 | 5/2002 | Forde et al. |
| 2002/0055769 A1 | 5/2002 | Wang |
| 2002/0058995 A1 | 5/2002 | Stevens |
| 2002/0077696 A1 | 6/2002 | Zadno-Azizi et al. |
| 2002/0082609 A1 | 6/2002 | Green |
| 2002/0095173 A1 | 7/2002 | Mazzocchi et al. |
| 2002/0095209 A1 | 7/2002 | Ladno-Azizi et al. |
| 2002/0111674 A1 | 8/2002 | Chouinard et al. |
| 2002/0120328 A1 | 8/2002 | Pathak et al. |
| 2002/0123802 A1 | 9/2002 | Snyders |
| 2002/0138138 A1 | 9/2002 | Yang |
| 2002/0151970 A1 | 10/2002 | Garrison et al. |
| 2002/0161390 A1 | 10/2002 | Mouw |
| 2002/0161392 A1 | 10/2002 | Dubrul |
| 2002/0161394 A1 | 10/2002 | Macoviak et al. |
| 2002/0165576 A1 | 11/2002 | Boyle et al. |
| 2002/0177766 A1 | 11/2002 | Mogul |
| 2002/0183781 A1 | 12/2002 | Casey et al. |
| 2002/0188341 A1 | 12/2002 | Elliott |
| 2002/0188344 A1 | 12/2002 | Bolea et al. |
| 2002/0193871 A1 | 12/2002 | Beyersdorf et al. |
| 2003/0014104 A1 | 1/2003 | Cribier |
| 2003/0023303 A1 | 1/2003 | Palmaz et al. |
| 2003/0028247 A1 | 2/2003 | Cali |
| 2003/0036791 A1 | 2/2003 | Philipp et al. |
| 2003/0040736 A1 | 2/2003 | Stevens et al. |
| 2003/0040771 A1 | 2/2003 | Hyodoh et al. |
| 2003/0040772 A1 | 2/2003 | Hyodoh et al. |
| 2003/0040791 A1 | 2/2003 | Oktay |
| 2003/0040792 A1 | 2/2003 | Gabbay |
| 2003/0050694 A1 | 3/2003 | Yang et al. |
| 2003/0055495 A1 | 3/2003 | Pease et al. |
| 2003/0057156 A1 | 3/2003 | Peterson et al. |
| 2003/0060844 A1 | 3/2003 | Borillo et al. |
| 2003/0069492 A1 | 4/2003 | Abrams et al. |
| 2003/0069646 A1 | 4/2003 | Stinson |
| 2003/0070944 A1 | 4/2003 | Nigam |
| 2003/0100918 A1 | 5/2003 | Duane |
| 2003/0100919 A1 | 5/2003 | Hopkins et al. |
| 2003/0109924 A1 | 6/2003 | Cribier |
| 2003/0109930 A1 | 6/2003 | Bluni et al. |
| 2003/0114912 A1 | 6/2003 | Sequin et al. |
| 2003/0114913 A1 | 6/2003 | Spenser et al. |
| 2003/0125795 A1 | 7/2003 | Pavcnik et al. |
| 2003/0130729 A1 | 7/2003 | Paniagua et al. |
| 2003/0135257 A1 | 7/2003 | Taheri |
| 2003/0144732 A1 | 7/2003 | Cosgrove et al. |
| 2003/0149475 A1 | 8/2003 | Hyodoh et al. |
| 2003/0149476 A1 | 8/2003 | Damm et al. |
| 2003/0149478 A1 | 8/2003 | Figulla et al. |
| 2003/0153974 A1 | 8/2003 | Spenser et al. |
| 2003/0171803 A1 | 9/2003 | Shimon |
| 2003/0176884 A1 | 9/2003 | Berrada et al. |
| 2003/0181850 A1 | 9/2003 | Diamond et al. |
| 2003/0187495 A1 | 10/2003 | Cully et al. |
| 2003/0191516 A1 | 10/2003 | Weldon et al. |
| 2003/0195609 A1 | 10/2003 | Berenstein et al. |
| 2003/0199759 A1 | 10/2003 | Richard |
| 2003/0199913 A1 | 10/2003 | Dubrul et al. |
| 2003/0199971 A1 | 10/2003 | Tower et al. |
| 2003/0199972 A1 | 10/2003 | Ladno-Azizi et al. |
| 2003/0208224 A1 | 11/2003 | Broome |
| 2003/0212429 A1 | 11/2003 | Keegan et al. |
| 2003/0212452 A1 | 11/2003 | Zadno-Azizi et al. |
| 2003/0212454 A1 | 11/2003 | Scott et al. |
| 2003/0216774 A1 | 11/2003 | Larson |
| 2003/0225445 A1 | 12/2003 | Derus et al. |
| 2003/0229390 A1 | 12/2003 | Ashton et al. |
| 2003/0233117 A1 | 12/2003 | Adams et al. |
| 2004/0019374 A1 | 1/2004 | Hojeibane et al. |
| 2004/0034411 A1 | 2/2004 | Quijano et al. |
| 2004/0039436 A1 | 2/2004 | Spenser et al. |
| 2004/0049224 A1 | 3/2004 | Buehlmann et al. |
| 2004/0049226 A1 | 3/2004 | Keegan et al. |
| 2004/0049262 A1 | 3/2004 | Obermiller et al. |
| 2004/0049266 A1 | 3/2004 | Anduiza et al. |
| 2004/0059409 A1 | 3/2004 | Stenzel |
| 2004/0073198 A1 | 4/2004 | Gilson et al. |
| 2004/0082904 A1 | 4/2004 | Houde et al. |
| 2004/0082967 A1 | 4/2004 | Broome et al. |
| 2004/0087982 A1 | 5/2004 | Eskuri |
| 2004/0088045 A1 | 5/2004 | Cox |
| 2004/0093016 A1 | 5/2004 | Root et al. |
| 2004/0093060 A1 | 5/2004 | Seguin et al. |
| 2004/0097788 A1 | 5/2004 | Mourlas et al. |
| 2004/0098022 A1 | 5/2004 | Barone |
| 2004/0098098 A1 | 5/2004 | McGuckin, Jr. et al. |
| 2004/0098099 A1 | 5/2004 | McCullagh et al. |
| 2004/0098112 A1 | 5/2004 | DiMatteo et al. |
| 2004/0107004 A1 | 6/2004 | Levine et al. |
| 2004/0111096 A1 | 6/2004 | Tu et al. |
| 2004/0116951 A1 | 6/2004 | Rosengart |
| 2004/0117004 A1 | 6/2004 | Osborne et al. |
| 2004/0117009 A1 | 6/2004 | Cali et al. |
| 2004/0122468 A1 | 6/2004 | Yodfat et al. |
| 2004/0122516 A1 | 6/2004 | Fogarty et al. |

(56) References Cited

U.S. PATENT DOCUMENTS

| | | |
|---|---|---|
| 2004/0127936 A1 | 7/2004 | Salahieh et al. |
| 2004/0127979 A1 | 7/2004 | Wilson et al. |
| 2004/0133274 A1 | 7/2004 | Webler et al. |
| 2004/0138694 A1 | 7/2004 | Tran et al. |
| 2004/0138742 A1 | 7/2004 | Myers et al. |
| 2004/0138743 A1 | 7/2004 | Myers et al. |
| 2004/0148018 A1 | 7/2004 | Carpentier et al. |
| 2004/0148021 A1 | 7/2004 | Cartledge et al. |
| 2004/0153094 A1 | 8/2004 | Dunfee et al. |
| 2004/0158277 A1 | 8/2004 | Lowe et al. |
| 2004/0167565 A1 | 8/2004 | Beulke et al. |
| 2004/0167620 A1 | 8/2004 | Ortiz et al. |
| 2004/0181140 A1 | 9/2004 | Falwell et al. |
| 2004/0186558 A1 | 9/2004 | Pavcnik et al. |
| 2004/0186563 A1 | 9/2004 | Lobbi |
| 2004/0193261 A1 | 9/2004 | Berreklouw |
| 2004/0199245 A1 | 10/2004 | Lauterjung |
| 2004/0204755 A1 | 10/2004 | Robin |
| 2004/0210304 A1 | 10/2004 | Seguin et al. |
| 2004/0210306 A1 | 10/2004 | Quijano et al. |
| 2004/0210307 A1 | 10/2004 | Khairkhahan |
| 2004/0215331 A1 | 10/2004 | Chew et al. |
| 2004/0215333 A1 | 10/2004 | Duran et al. |
| 2004/0215339 A1 | 10/2004 | Drasler et al. |
| 2004/0220655 A1 | 11/2004 | Swanson et al. |
| 2004/0225321 A1 | 11/2004 | Krolik et al. |
| 2004/0225353 A1 | 11/2004 | McGuckin, Jr. et al. |
| 2004/0225354 A1 | 11/2004 | Allen et al. |
| 2004/0225355 A1 | 11/2004 | Stevens |
| 2004/0243221 A1 | 12/2004 | Fawzi et al. |
| 2004/0254636 A1 | 12/2004 | Flagle et al. |
| 2004/0260390 A1 | 12/2004 | Sarac et al. |
| 2005/0010287 A1 | 1/2005 | Macoviak et al. |
| 2005/0021136 A1 | 1/2005 | Xie et al. |
| 2005/0033398 A1 | 2/2005 | Seguin |
| 2005/0033402 A1 | 2/2005 | Cully et al. |
| 2005/0043711 A1 | 2/2005 | Corcoran et al. |
| 2005/0043757 A1 | 2/2005 | Arad et al. |
| 2005/0043790 A1 | 2/2005 | Seguin |
| 2005/0049692 A1 | 3/2005 | Numamoto et al. |
| 2005/0049696 A1 | 3/2005 | Siess et al. |
| 2005/0055088 A1 | 3/2005 | Liddicoat et al. |
| 2005/0060016 A1 | 3/2005 | Wu et al. |
| 2005/0060029 A1 | 3/2005 | Le et al. |
| 2005/0065594 A1 | 3/2005 | DiMatteo et al. |
| 2005/0075584 A1 | 4/2005 | Cali |
| 2005/0075662 A1 | 4/2005 | Pedersen et al. |
| 2005/0075712 A1 | 4/2005 | Biancucci et al. |
| 2005/0075717 A1 | 4/2005 | Nguyen et al. |
| 2005/0075719 A1 | 4/2005 | Bergheim |
| 2005/0075724 A1 | 4/2005 | Svanidze et al. |
| 2005/0075730 A1 | 4/2005 | Myers et al. |
| 2005/0075731 A1 | 4/2005 | Artof et al. |
| 2005/0085841 A1 | 4/2005 | Eversull et al. |
| 2005/0085842 A1 | 4/2005 | Eversull et al. |
| 2005/0085843 A1 | 4/2005 | Opolski et al. |
| 2005/0085890 A1 | 4/2005 | Rasmussen et al. |
| 2005/0090846 A1 | 4/2005 | Pedersen et al. |
| 2005/0090890 A1 | 4/2005 | Wu et al. |
| 2005/0096692 A1 | 5/2005 | Linder et al. |
| 2005/0096734 A1 | 5/2005 | Majercak et al. |
| 2005/0096735 A1 | 5/2005 | Hojeibane et al. |
| 2005/0096736 A1 | 5/2005 | Osse et al. |
| 2005/0096738 A1 | 5/2005 | Cali et al. |
| 2005/0100580 A1 | 5/2005 | Osborne et al. |
| 2005/0107822 A1 | 5/2005 | Wasdyke |
| 2005/0113910 A1 | 5/2005 | Paniagua et al. |
| 2005/0131438 A1 | 6/2005 | Cohn |
| 2005/0137683 A1 | 6/2005 | Hezi-Yamit et al. |
| 2005/0137686 A1 | 6/2005 | Salahieh et al. |
| 2005/0137687 A1* | 6/2005 | Salahieh ............... A61F 2/2418 623/2.11 |
| 2005/0137688 A1 | 6/2005 | Salahieh et al. |
| 2005/0137689 A1 | 6/2005 | Salahieh et al. |
| 2005/0137690 A1 | 6/2005 | Salahieh et al. |
| 2005/0137691 A1 | 6/2005 | Salahieh et al. |
| 2005/0137692 A1 | 6/2005 | Haug et al. |
| 2005/0137693 A1 | 6/2005 | Haug et al. |
| 2005/0137694 A1 | 6/2005 | Haug et al. |
| 2005/0137695 A1 | 6/2005 | Salahieh et al. |
| 2005/0137696 A1 | 6/2005 | Salahieh et al. |
| 2005/0137697 A1 | 6/2005 | Salahieh et al. |
| 2005/0137698 A1 | 6/2005 | Salahieh et al. |
| 2005/0137699 A1 | 6/2005 | Salahieh et al. |
| 2005/0137701 A1 | 6/2005 | Salahieh et al. |
| 2005/0137702 A1 | 6/2005 | Haug et al. |
| 2005/0143807 A1 | 6/2005 | Pavcnik et al. |
| 2005/0143809 A1 | 6/2005 | Salahieh et al. |
| 2005/0149159 A1 | 7/2005 | Andreas et al. |
| 2005/0165352 A1 | 7/2005 | Henry et al. |
| 2005/0165477 A1 | 7/2005 | Anduiza et al. |
| 2005/0165479 A1 | 7/2005 | Drews et al. |
| 2005/0182486 A1 | 8/2005 | Gabbay |
| 2005/0197694 A1 | 9/2005 | Pai et al. |
| 2005/0197695 A1 | 9/2005 | Stacchino et al. |
| 2005/0203549 A1 | 9/2005 | Realyvasquez |
| 2005/0203614 A1 | 9/2005 | Forster et al. |
| 2005/0203615 A1 | 9/2005 | Forster et al. |
| 2005/0203616 A1 | 9/2005 | Cribier |
| 2005/0203617 A1 | 9/2005 | Forster et al. |
| 2005/0203618 A1 | 9/2005 | Sharkawy et al. |
| 2005/0209580 A1 | 9/2005 | Freyman |
| 2005/0228472 A1 | 10/2005 | Case et al. |
| 2005/0228495 A1 | 10/2005 | Macoviak |
| 2005/0234546 A1 | 10/2005 | Nugent et al. |
| 2005/0240200 A1 | 10/2005 | Bergheim |
| 2005/0240262 A1 | 10/2005 | White |
| 2005/0251250 A1 | 11/2005 | Verhoeven et al. |
| 2005/0251251 A1 | 11/2005 | Cribier |
| 2005/0261759 A1 | 11/2005 | Lambrecht et al. |
| 2005/0267560 A1 | 12/2005 | Bates |
| 2005/0283231 A1 | 12/2005 | Haug et al. |
| 2005/0283962 A1 | 12/2005 | Boudjemline |
| 2006/0004439 A1 | 1/2006 | Spenser et al. |
| 2006/0004442 A1 | 1/2006 | Spenser et al. |
| 2006/0015168 A1 | 1/2006 | Gunderson |
| 2006/0058872 A1 | 3/2006 | Salahieh et al. |
| 2006/0149360 A1 | 7/2006 | Schwammenthal et al. |
| 2006/0155312 A1 | 7/2006 | Levine et al. |
| 2006/0161249 A1 | 7/2006 | Realyvasquez et al. |
| 2006/0173524 A1 | 8/2006 | Salahieh et al. |
| 2006/0195183 A1 | 8/2006 | Navia et al. |
| 2006/0253191 A1 | 11/2006 | Salahieh et al. |
| 2006/0259134 A1 | 11/2006 | Schwammenthal et al. |
| 2006/0271166 A1 | 11/2006 | Thill et al. |
| 2006/0287668 A1 | 12/2006 | Fawzi et al. |
| 2006/0287717 A1 | 12/2006 | Rowe et al. |
| 2007/0010876 A1 | 1/2007 | Salahieh et al. |
| 2007/0010877 A1 | 1/2007 | Salahieh et al. |
| 2007/0016286 A1 | 1/2007 | Herrmann et al. |
| 2007/0055340 A1 | 3/2007 | Pryor |
| 2007/0061008 A1 | 3/2007 | Salahieh et al. |
| 2007/0088431 A1* | 4/2007 | Bourang ............... A61F 2/2433 623/2.11 |
| 2007/0112355 A1 | 5/2007 | Salahieh et al. |
| 2007/0118214 A1 | 5/2007 | Salahieh et al. |
| 2007/0162107 A1 | 7/2007 | Haug et al. |
| 2007/0173918 A1 | 7/2007 | Dreher et al. |
| 2007/0203503 A1 | 8/2007 | Salahieh et al. |
| 2007/0244552 A1 | 10/2007 | Salahieh et al. |
| 2007/0288089 A1 | 12/2007 | Gurskis et al. |
| 2008/0009940 A1 | 1/2008 | Cribier |
| 2008/0033541 A1 | 2/2008 | Gelbart et al. |
| 2008/0082165 A1 | 4/2008 | Wilson et al. |
| 2008/0125859 A1 | 5/2008 | Salahieh et al. |
| 2008/0188928 A1 | 8/2008 | Salahieh et al. |
| 2008/0208328 A1 | 8/2008 | Antocci et al. |
| 2008/0208332 A1 | 8/2008 | Lamphere et al. |
| 2008/0221672 A1 | 9/2008 | Lamphere et al. |
| 2008/0234814 A1 | 9/2008 | Salahieh et al. |
| 2008/0255661 A1 | 10/2008 | Straubinger et al. |
| 2008/0269878 A1 | 10/2008 | Iobbi |
| 2008/0288054 A1 | 11/2008 | Pulnev et al. |
| 2009/0005863 A1 | 1/2009 | Goetz et al. |

(56) References Cited

U.S. PATENT DOCUMENTS

| | | |
|---|---|---|
| 2009/0030512 A1 | 1/2009 | Thielen et al. |
| 2009/0054969 A1 | 2/2009 | Salahieh et al. |
| 2009/0076598 A1 | 3/2009 | Salahieh et al. |
| 2009/0093877 A1 | 4/2009 | Keidar et al. |
| 2009/0099640 A1 | 4/2009 | Weng |
| 2009/0171456 A1 | 7/2009 | Kveen et al. |
| 2009/0222076 A1 | 9/2009 | Figulla et al. |
| 2009/0264759 A1 | 10/2009 | Byrd |
| 2009/0264997 A1 | 10/2009 | Salahieh et al. |
| 2009/0299462 A1 | 12/2009 | Fawzi et al. |
| 2010/0049313 A1 | 2/2010 | Alon et al. |
| 2010/0094399 A1 | 4/2010 | Dorn et al. |
| 2010/0121434 A1 | 5/2010 | Paul et al. |
| 2010/0191326 A1 | 7/2010 | Alkhatib |
| 2010/0219092 A1 | 9/2010 | Salahieh et al. |
| 2010/0280495 A1 | 11/2010 | Paul et al. |
| 2011/0257735 A1 | 10/2011 | Salahieh et al. |
| 2011/0276129 A1 | 11/2011 | Salahieh et al. |
| 2012/0016469 A1 | 1/2012 | Salahieh et al. |
| 2012/0016471 A1 | 1/2012 | Salahieh et al. |
| 2012/0022642 A1 | 1/2012 | Haug et al. |
| 2012/0029627 A1 | 2/2012 | Salahieh et al. |
| 2012/0041549 A1 | 2/2012 | Salahieh et al. |
| 2012/0041550 A1 | 2/2012 | Salahieh et al. |
| 2012/0046740 A1 | 2/2012 | Paul et al. |
| 2012/0053683 A1 | 3/2012 | Salahieh et al. |
| 2012/0089224 A1 | 4/2012 | Haug et al. |
| 2012/0132547 A1 | 5/2012 | Salahieh et al. |
| 2012/0197379 A1 | 8/2012 | Laske et al. |
| 2012/0330409 A1 | 12/2012 | Haug et al. |
| 2013/0013057 A1 | 1/2013 | Salahieh et al. |
| 2013/0018457 A1 | 1/2013 | Gregg et al. |
| 2013/0030520 A1 | 1/2013 | Lee et al. |
| 2013/0123796 A1 | 5/2013 | Sutton et al. |
| 2013/0158656 A1 | 6/2013 | Sutton et al. |
| 2013/0190865 A1 | 7/2013 | Anderson |
| 2013/0197629 A1* | 8/2013 | Gainor .......... A61F 2/2439 623/2.11 |
| 2013/0304199 A1 | 11/2013 | Sutton et al. |
| 2014/0018911 A1 | 1/2014 | Zhou et al. |
| 2014/0094904 A1 | 4/2014 | Salahieh et al. |
| 2014/0114405 A1 | 4/2014 | Paul et al. |
| 2014/0114406 A1 | 4/2014 | Salahieh et al. |
| 2014/0121766 A1 | 5/2014 | Salahieh et al. |
| 2014/0135912 A1 | 5/2014 | Salahieh et al. |
| 2014/0243967 A1 | 8/2014 | Salahieh et al. |
| 2014/0296962 A1 | 10/2014 | Cartledge et al. |
| 2015/0127094 A1 | 5/2015 | Salahieh et al. |

FOREIGN PATENT DOCUMENTS

| | | |
|---|---|---|
| DE | 19546692 A1 | 6/1997 |
| DE | 19857887 A1 | 7/2000 |
| DE | 19907646 A1 | 8/2000 |
| DE | 10049812 A1 | 4/2002 |
| DE | 10049813 C1 | 4/2002 |
| DE | 10049814 A1 | 4/2002 |
| DE | 10049815 A1 | 4/2002 |
| EP | 0103546 B1 | 5/1988 |
| EP | 0144167 B1 | 11/1989 |
| EP | 0409929 B1 | 4/1997 |
| EP | 0850607 A1 | 7/1998 |
| EP | 0597967 B1 | 12/1999 |
| EP | 1000590 A1 | 5/2000 |
| EP | 1057459 A1 | 12/2000 |
| EP | 1057460 A1 | 12/2000 |
| EP | 1088529 A2 | 4/2001 |
| EP | 0937439 B1 | 9/2003 |
| EP | 1340473 A2 | 9/2003 |
| EP | 1356793 A2 | 10/2003 |
| EP | 1042045 B1 | 5/2004 |
| EP | 0819013 B1 | 6/2004 |
| EP | 1430853 A2 | 6/2004 |
| EP | 1472996 A1 | 11/2004 |
| EP | 1229864 B1 | 4/2005 |
| EP | 1059894 B1 | 7/2005 |
| EP | 1078610 B1 | 8/2005 |
| EP | 1570809 A1 | 9/2005 |
| EP | 1576937 A2 | 9/2005 |
| EP | 1582178 A2 | 10/2005 |
| EP | 1582179 A2 | 10/2005 |
| EP | 1469797 B1 | 11/2005 |
| EP | 1600121 A1 | 11/2005 |
| EP | 1156757 B1 | 12/2005 |
| EP | 1616531 A2 | 1/2006 |
| EP | 1605871 B1 | 7/2008 |
| FR | 2788217 A1 | 7/2000 |
| GB | 2056023 A | 3/1981 |
| GB | 2398245 A | 8/2004 |
| SU | 1271508 A1 | 11/1986 |
| SU | 1371700 A1 | 2/1988 |
| WO | 9117720 A1 | 11/1991 |
| WO | 9217118 A1 | 10/1992 |
| WO | 9301768 A1 | 2/1993 |
| WO | 9315693 A1 | 8/1993 |
| WO | 9504556 A2 | 2/1995 |
| WO | 9529640 A1 | 11/1995 |
| WO | 9614032 A1 | 5/1996 |
| WO | 9624306 A1 | 8/1996 |
| WO | 9640012 A1 | 12/1996 |
| WO | 9829057 A1 | 7/1998 |
| WO | 9836790 A1 | 8/1998 |
| WO | 9850103 A1 | 11/1998 |
| WO | 9857599 A2 | 12/1998 |
| WO | 9933414 A1 | 7/1999 |
| WO | 9940964 A1 | 8/1999 |
| WO | 9944542 A2 | 9/1999 |
| WO | 9947075 A1 | 9/1999 |
| WO | 0009059 A2 | 2/2000 |
| WO | 0041652 A1 | 7/2000 |
| WO | 0044308 A2 | 8/2000 |
| WO | 0044311 A2 | 8/2000 |
| WO | 0044313 A1 | 8/2000 |
| WO | 0045874 A1 | 8/2000 |
| WO | 0047139 A1 | 8/2000 |
| WO | 0049970 A1 | 8/2000 |
| WO | 0067661 A2 | 11/2000 |
| WO | 0105331 A1 | 1/2001 |
| WO | 0108596 A1 | 2/2001 |
| WO | 0110320 A1 | 2/2001 |
| WO | 0110343 A1 | 2/2001 |
| WO | 0135870 A1 | 5/2001 |
| WO | 0149213 A2 | 7/2001 |
| WO | 0154625 A1 | 8/2001 |
| WO | 0162189 A1 | 8/2001 |
| WO | 0164137 A1 | 9/2001 |
| WO | 0176510 A2 | 10/2001 |
| WO | 0197715 A1 | 12/2001 |
| WO | 0236048 A1 | 5/2002 |
| WO | 0241789 A2 | 5/2002 |
| WO | 0243620 A1 | 6/2002 |
| WO | 0247575 A2 | 6/2002 |
| WO | 02056955 A1 | 7/2002 |
| WO | 02100297 A2 | 12/2002 |
| WO | 03003943 A2 | 1/2003 |
| WO | 03003949 A1 | 1/2003 |
| WO | 03011195 A2 | 2/2003 |
| WO | 03028592 A1 | 4/2003 |
| WO | 03030776 A2 | 4/2003 |
| WO | 03037227 A2 | 5/2003 |
| WO | 03047648 A2 | 6/2003 |
| WO | 03015851 B1 | 11/2003 |
| WO | 03094793 A1 | 11/2003 |
| WO | 03094797 A1 | 11/2003 |
| WO | 2004006803 A1 | 1/2004 |
| WO | 2004006804 A1 | 1/2004 |
| WO | 2004014256 A1 | 2/2004 |
| WO | 2004019811 A2 | 3/2004 |
| WO | 2004019817 A1 | 3/2004 |
| WO | 2004021922 A2 | 3/2004 |
| WO | 2004023980 A2 | 3/2004 |
| WO | 2004026117 A2 | 4/2004 |
| WO | 2004041126 A1 | 5/2004 |

(56) References Cited

FOREIGN PATENT DOCUMENTS

| | | | |
|---|---|---|---|
| WO | 2004043293 A2 | 5/2004 |
| WO | 2004047681 A1 | 6/2004 |
| WO | 2004058106 A2 | 7/2004 |
| WO | 2004066876 A1 | 8/2004 |
| WO | 2004082536 A1 | 9/2004 |
| WO | 2004089250 A1 | 10/2004 |
| WO | 2004089253 A1 | 10/2004 |
| WO | 2004093728 A2 | 11/2004 |
| WO | 2004105651 A1 | 12/2004 |
| WO | 2005002466 A2 | 1/2005 |
| WO | 2005004753 A1 | 1/2005 |
| WO | 2005009285 A2 | 2/2005 |
| WO | 2005011534 A1 | 2/2005 |
| WO | 2005011535 A2 | 2/2005 |
| WO | 2005023155 A1 | 3/2005 |
| WO | 2005027790 A1 | 3/2005 |
| WO | 2005046528 A1 | 5/2005 |
| WO | 2005046529 A1 | 5/2005 |
| WO | 2005048883 A1 | 6/2005 |
| WO | 2005062980 A2 | 7/2005 |
| WO | 2005065585 A1 | 7/2005 |
| WO | 2005084595 A1 | 9/2005 |
| WO | 2005087140 A1 | 9/2005 |
| WO | 2005096993 A1 | 10/2005 |
| WO | 2006005015 A2 | 1/2006 |
| WO | 2006009690 A1 | 1/2006 |
| WO | 2006027499 A2 | 3/2006 |
| WO | 2006037086 A1 | 4/2006 |
| WO | 2006138391 A2 | 12/2006 |
| WO | 2007033093 A2 | 3/2007 |
| WO | 2007035471 A2 | 3/2007 |
| WO | 2007044285 A2 | 4/2007 |
| WO | 2007053243 A2 | 4/2007 |
| WO | 2007058847 A2 | 5/2007 |
| WO | 2007092354 A2 | 8/2007 |
| WO | 2007097983 A2 | 8/2007 |
| WO | 2010042950 A2 | 4/2010 |
| WO | 2012116368 A2 | 8/2012 |
| WO | 2013009975 A1 | 1/2013 |
| WO | 2013028387 A2 | 2/2013 |
| WO | 2013096545 A1 | 6/2013 |
| WO | 2016126511 A2 | 8/2016 |

OTHER PUBLICATIONS

Atwood et al., "Insertion of Heart Valves by Catheterization." Project Supervised by Prof. S. Muftu of Northeastern University 2001-2002: 36-40, May 30, 2002.
Bodnar et al., "Replacement Cardiac Valves R Chapter 13: Extinct Cardiac Valve Prostheses." Pergamon Publishing Corporation. New York, 307-322, 1991.
Boudjemline et al., "Percutaneous Implantation of a Biological Valve in the Aorta to Treat Aortic Valve Insufficiency—A Sheep Study." Med Sci. Monit., vol. 8, No. 4: BR113-116, Apr. 12, 2002.
Boudjemline et al., "Percutaneous Implantation of a Valve in the Descending Aorta in Lambs." Euro. Heart J., 23: 1045-1049, Jul. 2002.
Boudjemline et al., "Percutaneous Pulmonary Valve Replacement in a Large Right Ventricular Outflow Tract: An Experimental Study." Journal of the American College of Cardiology, vol. 43(6): 1082-1087, Mar. 17, 2004.
Boudjemline et al., "Percutaneous Valve Insertion: A New Approach?" J. of Thoracic and Cardio. Surg, 125(3): 741-743, Mar. 2003.
Boudjemline et al., "Steps Toward Percutaneous Aortic Valve Replacement." Circulation, 105: 775-778, Feb. 12, 2002.
Cribier et al., "Early Experience with Percutaneous Transcatheter Implantation of Heart Valve Prosthesis for the Treatment of End-Stage Inoperable Patients with Calcific Aortic Stenosis." J. of Am. Coll. of Cardio, 43(4): 698-703, Feb. 18, 2004.
Cribier et al., "Percutaneous Transcatheter Implementation of an Aortic Valve Prosthesis for Calcitic Aortic Stenosis: First Human Case Description." Circulation, 106: 3006-3008, Dec. 10, 2002.

Cribier et al., "Percutaneous Transcatheter Implantation of an Aortic Valve Prosthesis for Calcific Aortic Stenosis: First Human Case." Percutaneous Valve Technologies, Inc., 16 pages, Apr. 16, 2002.
Ferrari et al., "Percutaneous Transvascular Aortic Valve Replacement with Self-Expanding Stent-Valve Device." Poster from the presentation given at SMIT 2000, 12th International Conference. Sep. 5, 2000.
Hijazi, "Transcatheter Valve Replacement: A New Era of Percutaneous Cardiac Intervention Begins." J. of Am. College of Cardio., 43(6): 1088-1089, Mar. 17, 2004.
Huber et al., "Do Valved Stents Compromise Coronary Flow?" European Journal of Cardio-thoracic Surgery, vol. 25: 754-759, Jan. 23, 2004.
Knudsen et al., "Catheter-implanted prosthetic heart valves." Int'l J. of Art. Organs, 16(5): 253-262, May 1993.
Kort et al., "Minimally Invasive Aortic Valve Replacement: Echocardiographic and Clinical Results." Am. Heart J., 142(3): 476-481, Sep. 2001.
Love et al., The Autogenous Tissue Heart Valve: Current Status. Journal of Cardiac Surgery, 6(4): 499-507, Mar. 1991.
Lutter et al., "Percutaneous Aortic Valve Replacement: An Experimental Study. I. Studies on Implantation." J. of Thoracic and Cardio. Surg., 123(4): 768-776, Apr. 2002.
Moulopoulos et al., "Catheter-Mounted Aortic Valves." Annals of Thoracic Surg., 11(5): 423-430, May 1971.
Paniagua et al., "Percutaneous Heart Valve in the Chronic in Vitro Testing Model." Circulation, 106: e51-e52, Sep. 17, 2002.
Paniagua et al., "Heart Watch." Texas Heart Institute. Edition: 8 pages, Spring, 2004.
Pavcnik et al., "Percutaneous Bioprosthetic Venous Valve: A Long-term Study in Sheep." J. of Vascular Surg., 35(3): 598-603, Mar. 2002.
Phillips et al., "A Temporary Catheter-Tip Aortic Valve: Hemodynamic Effects on Experimental Acute Aortic Insufficiency." Annals of Thoracic Surg., 21(2): 134-136, Feb. 1976.
Sochman et al., "Percutaneous Transcatheter Aortic Disc Valve Prosthesis Implantation: A Feasibility Study." Cardiovasc. Intervent. Radiol., 23: 384-388, Sep. 2000.
Stuart, "In Heart Valves, A Brave, New Non-Surgical World." Start-Up. Feb. 9-17, 2004.
Vahanian et al., "Percutaneous Approaches to Valvular Disease." Circulation, 109: 1572-1579, Apr. 6, 2004.
Van Herwerden et al., "Percutaneous Valve Implantation: Back to the Future?" Euro. Heart J., 23(18): 1415-1416, Sep. 2002.
Zhou et al, "Self-expandable Valved Stent of Large Size: Off-Bypass Implantation in Pulmonary Position." Eur. J. Cardiothorac, 24: 212-216, Aug. 2003.
Examiner's First Report on AU Patent Application No. 2011202667, dated May 17, 2012.
"A Matter of Size." Triennial Review of the National Nanotechnology Initiative, The National Academies Press, Washington DC, v-13, http://www.nap.edu/catalog/11752/a-matter-of-size-triennial-review-of-the-national-nanotechnology, 2006.
Atwood et al., "Insertion of Heart Valves by Catheterization." The Capstone Design Course Report MIME 1501-1502. Technical Design Report Northeastern University, pp. 1-93, Nov. 5, 2007.
Supplemental Search Report from EP Patent Office, EP Application No. 04813777.2, dated Aug. 19, 2011.
Supplemental Search Report from EP Patent Office, EP Application No. 04815634.3, dated Aug. 19, 2011.
Cunanan et al., "Tissue Characterization and Calcification Potential of Commercial Bioprosthetic Heart Valves." Ann. Thorac. Surg., S417-421, May 15, 2001.
Cunliffe et al., "Glutaraldehyde Inactivation of Exotic Animal Viruses in Swine Heart Tissue." Applied and Environmental Microbiology, Greenport, New York, 37(5): 1044-1046, May 1979.
EP Search Report for EP Application No. 06824992.9, dated Aug. 10, 2011.
"Heart Valve Materials—Bovine (cow)." Equine & Porcine Pericardium, Maverick Biosciences Pty. Lt, http://maverickbio.com/biological-medical-device-materials.php?htm. 2009.

(56) References Cited

OTHER PUBLICATIONS

Helmus, "Mechanical and Bioprosthetic Heart Valves in Biomaterials for Artificial Organs." Woodhead Publishing Limited: 114-162, 2011.

Hourihan et al., "Transcatheter Umbrella Closure of Valvular and Paravalvular Leaks." JACC, Boston, Massachusetts, 20(6): 1371-1377, Nov. 15, 1992.

Laborde et al., "Percutaneous Implantation of the Corevalve Aortic Valve Prosthesis for Patients Presenting High Risk for Surgical Valve Replacement." EuroIntervention: 472-474, Feb. 2006.

Levy, "*Mycobacterium chelonei* Infection of Porcine Heart Valves." The New England Journal of Medicine, Washington DC, 297(12), Sep. 22, 1977.

Supplemental Search Report from EP Patent Office, EP Application No. 05758878.2, dated Oct. 24, 2011.

"Pericardial Heart Valves." Edwards Lifesciences, Cardiovascular Surgery FAQ, http://www.edwards.com/products/cardiovascularsurgeryfaq.htm, Nov. 14, 2010.

Southern Lights Biomaterials Homepage, http://www.slv.co.nz/, Jan. 7, 2011.

Stassano. "Mid-term Results of the Valve-on-Valve Technique for Bioprosthetic Failure." European Journal of Cardiothoracic Surgery: vol. 18, 453-457, Oct. 2000.

Topol. "Percutaneous Expandable Prosthetic Valves." Textbook of Interventional Cardiology, W.B. Saunders Company, 2: 1268-1276, 1994.

International Search Report and Written Opinion dated Apr. 11, 2017 for International Application No. PCT/US2017/015629.

\* cited by examiner

TENSIONED SHEATHING AIDS

RELATED APPLICATIONS

This application claims the benefit of U.S. Provisional Application Ser. No. 62/289,993, filed Feb. 2, 2016.

TECHNICAL FIELD

The present disclosure pertains to medical devices, and methods for manufacturing and/or using medical devices. More particularly, the present disclosure pertains to sheathing aids for a medical device and/or a replacement heart valve.

BACKGROUND

A wide variety of intracorporeal medical devices have been developed for medical use, for example, intravascular use. Some of these devices include guidewires, catheters, medical device delivery systems (e.g., for stents, grafts, replacement valves, etc.), and the like. These devices are manufactured by any one of a variety of different manufacturing methods and may be used according to any one of a variety of methods. Of the known medical devices and methods, each has certain advantages and disadvantages. There is an ongoing need to provide alternative medical devices as well as alternative methods for manufacturing and using medical devices.

SUMMARY

In a first aspect, a medical device apparatus may comprise a medical implant including a braided anchor member operatively connected to a delivery system, the delivery system including a handle, an outer sheath extending distally from the handle, and an inner catheter disposed within the outer sheath, and a sheathing aid connecting the delivery system to the medical implant, the sheathing aid being configured to guide the medical implant into the outer sheath upon relative closing movement therebetween. The sheathing aid may include a plurality of filaments extending from the inner catheter to a proximal end of the braided anchor member, and a cleat disc disposed within a coupler ring fixedly attached to a distal end of the inner catheter. The plurality of filaments may be releasably coupled to the cleat disc.

In addition or alternatively, and in a second aspect, the cleat disc is movably disposed within the coupler ring.

In addition or alternatively, and in a third aspect, the cleat disc includes one or more cleat posts extending distally from the cleat disc.

In addition or alternatively, and in a fourth aspect, the plurality of filaments is releasably coupled to the one or more cleat posts.

In addition or alternatively, and in a fifth aspect, the one or more cleat posts comprises three cleat posts.

In addition or alternatively, and in a sixth aspect, the inner catheter includes a plurality of fingers extending distally from the coupler ring, the plurality of fingers being releasably coupled to the medical implant.

In addition or alternatively, and in a seventh aspect, the plurality of filaments extend through one or more openings disposed within a side wall of the coupler ring.

In addition or alternatively, and in an eighth aspect, at least some of the plurality of filaments each include a tubular member disposed thereon between the inner catheter and the medical implant.

In addition or alternatively, and in a ninth aspect, the at least some of the plurality of filaments comprises all of the plurality of filaments.

In addition or alternatively, and in a tenth aspect, each tubular member has a length, the length of all of the tubular members being substantially similar.

In addition or alternatively, and in an eleventh aspect, the tubular members have varying lengths.

In addition or alternatively, and in a twelfth aspect, the delivery system includes at least one actuator element extending from the inner catheter to the medical implant, the at least one actuator element being configured to reversibly shift the braided anchor member from an elongated delivery configuration to an enlarged deployed configuration.

In addition or alternatively, and in a thirteenth aspect, each of the at least one actuator element passes through the cleat disc.

In addition or alternatively, and in a fourteenth aspect, each of the at least one actuator element includes a tubular sleeve disposed thereon and extending between the cleat disc and the medical implant.

In addition or alternatively, and in a fifteenth aspect, each of the at least one actuator element includes an enlarged portion disposed between the cleat disc and the medical implant.

In addition or alternatively, and in a sixteenth aspect, proximal translation of the at least one actuator element moves the cleat disc proximally after the braided anchor member has been shifted to the enlarged deployed configuration.

In addition or alternatively, and in a seventeenth aspect, moving the cleat disc proximally releases the plurality of filaments from the cleat disc.

In addition or alternatively, and in an eighteenth aspect, the braided anchor member includes a plurality of crowns, wherein each of the plurality of filaments is releasably attached at one of the plurality of crowns.

In addition or alternatively, and in a nineteenth aspect, a medical device apparatus may comprise a medical implant including an anchor member configured to actuate between a delivery configuration and a deployed configuration operatively connected to a delivery system, the delivery system including a handle, an outer sheath extending distally from the handle, and an inner catheter disposed within the outer sheath, and a sheathing aid connecting the delivery system to the medical implant, the sheathing aid being configured to guide the medical implant into the outer sheath upon relative closing movement therebetween. The sheathing aid may include a plurality of tethers extending from the inner catheter to a proximal end of the anchor member, and a release mechanism slidably disposed within a coupler ring coupled to a distal end of the inner catheter. The plurality of tethers may be releasably coupled to the release mechanism.

In addition or alternatively, and in a twentieth aspect, a medical device apparatus may comprise a medical implant including a tubular anchoring structure configured to shift between an elongated configuration and an expanded configuration operatively connected to a delivery system, the delivery system including a handle, an outer sheath extending distally from the handle, and an inner catheter disposed within the outer sheath, and a sheathing aid connecting the delivery system to the medical implant, the sheathing aid being configured to guide the medical implant into the outer sheath upon relative closing movement therebetween. The sheathing aid may include a plurality of tensioning elements extending from the inner catheter to a proximal end of the tubular anchoring structure, and a release pin disposed within a coupler ring attached to a distal end of the inner catheter. The plurality of tensioning elements may be releasably coupled to the release pin.

The above summary of some embodiments, aspects, and/or examples is not intended to describe each disclosed embodiment or every implementation of the present disclosure. The Figures, and Detailed Description, which follow, more particularly exemplify these embodiments.

BRIEF DESCRIPTION OF THE DRAWINGS

The disclosure may be more completely understood in consideration of the following detailed description in connection with the accompanying drawings, in which.

Figure 1:
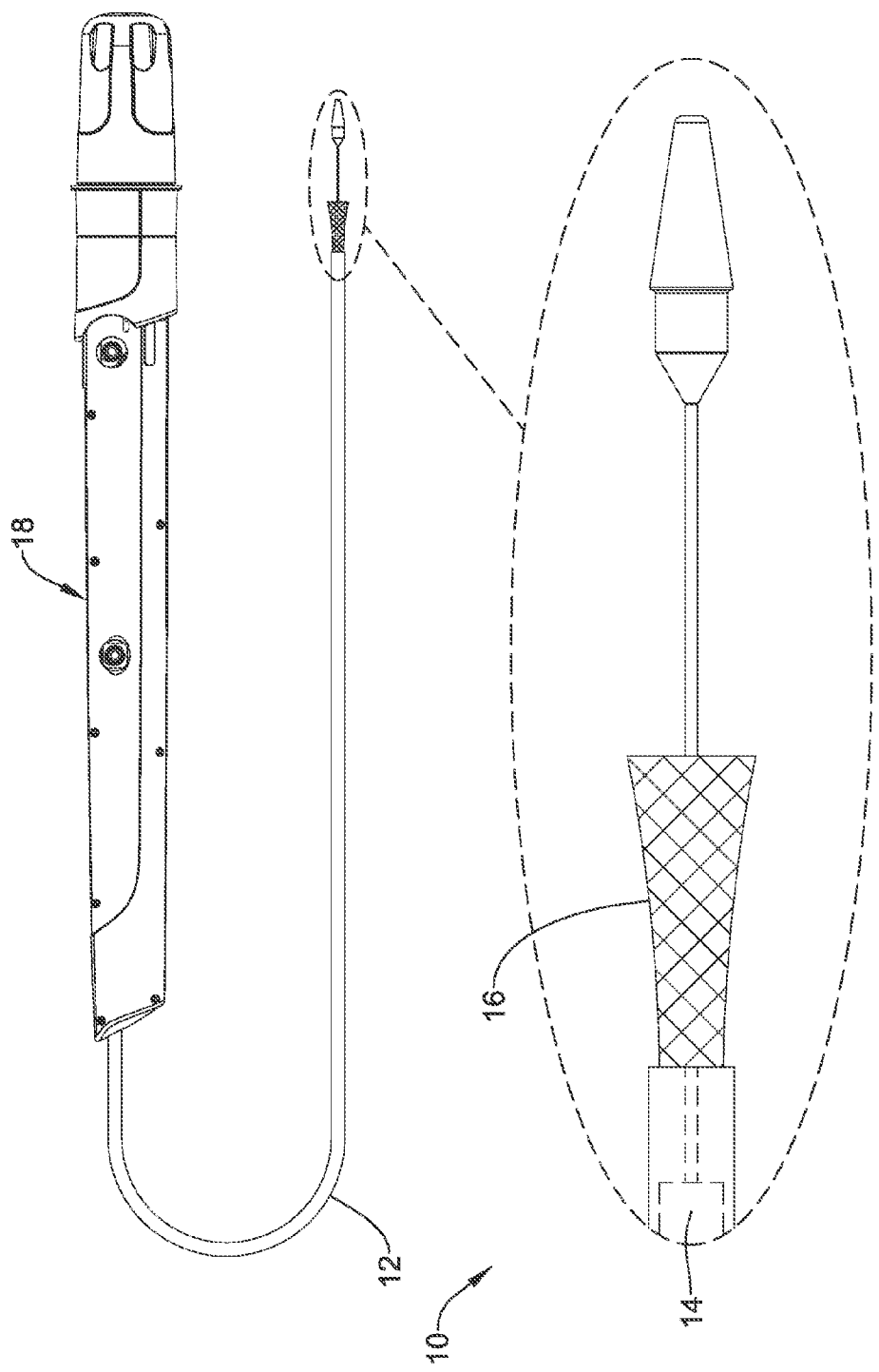
FIG. 1 illustrates an example medical device system.

While aspects of the disclosure are amenable to various modifications and alternative forms, specifics thereof have been shown by way of example in the drawings and will be described in detail. It should be understood, however, that the intention is not to limit aspects of the disclosure to the particular embodiments described. On the contrary, the intention is to cover all modifications, equivalents, and alternatives falling within the spirit and scope of the disclosure.

DETAILED DESCRIPTION

The following description should be read with reference to the drawings, which are not necessarily to scale, wherein like reference numerals indicate like elements throughout the several views. The detailed description and drawings are intended to illustrate but not limit the claimed invention. Those skilled in the art will recognize that the various elements described and/or shown may be arranged in various combinations and configurations without departing from the scope of the disclosure. The detailed description and drawings illustrate example embodiments of the claimed invention.

Generally speaking, in terms of the orientation of the structural elements relative to each other and the operation of the disclosed device(s), a proximal end may be considered closest to the user (or external to a patient) and a distal end farthest from the user (or internal to a patient). However, the skilled artisan will appreciate that the orientations and/or directions may be reversed as necessary or appropriate.

For the following defined terms, these definitions shall be applied, unless a different definition is given in the claims or elsewhere in this specification.

All numeric values are herein assumed to be modified by the term "about," whether or not explicitly indicated. The term "about", in the context of numeric values, generally refers to a range of numbers that one of skill in the art would consider equivalent to the recited value (i.e., having the same function or result). In many instances, the term "about" may include numbers that are rounded to the nearest significant figure. Other uses of the term "about" (i.e., in a context other than numeric values) may be assumed to have their ordinary and customary definition(s), as understood from and consistent with the context of the specification, unless otherwise specified.

The recitation of numerical ranges by endpoints includes all numbers within that range, including the endpoints (e.g. 1 to 5 includes 1, 1.5, 2, 2.75, 3, 3.80, 4, and 5).

Although some suitable dimensions, ranges and/or values pertaining to various components, features and/or specifications are disclosed, one of skill in the art, incited by the present disclosure, would understand desired dimensions, ranges and/or values may deviate from those expressly disclosed.

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

Relative terms such as "proximal", "distal", "advance", "retract", variants thereof, and the like, may be generally be considered with respect to the positioning, direction, and/or operation of various elements relative to a user/operator/manipulator of the device, wherein "proximal" and "retract" indicate or refer to closer to or toward the user and "distal" and "advance" indicate or refer to farther from or away from the user. Other relative terms, such as "upstream" and "downstream" refer to a direction of fluid flow within a lumen, such as a body lumen or blood vessel.

It is noted that references in the specification to "an embodiment", "some embodiments", "other embodiments", etc., indicate that the embodiment(s) described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it would be within the knowledge of one skilled in the art to effect such feature, structure, or characteristic in connection with other embodiments, whether or not explicitly described, unless clearly stated to the contrary. That is, the various individual elements described below, even if not explicitly shown in a particular combination, are nevertheless contemplated as being combinable or arrangable with each other to form other additional embodiments or to complement and/or enrich the described embodiment(s), as would be understood by one of ordinary skill in the art.

For the purpose of clarity, certain identifying numerical nomenclature (e.g., first, second, third, fourth, etc.) may be used throughout the description and/or claims to name and/or differentiate between various described and/or claimed features. It is to be understood that the numerical nomenclature is not intended to be limiting and is exemplary only. In some embodiments, alterations of and deviations from previously-used numerical nomenclature may be made in the interest of brevity and clarity. That is, a feature identified as a "first" element may later be referred to as a "second" element, a "third" element, etc. or may be omitted entirely, and/or a different feature may be referred to as the "first" element. The meaning and/or designation in each instance will be apparent to the skilled practitioner.

Diseases and/or medical conditions that impact the cardiovascular system are prevalent in the United States and throughout the world. Traditionally, treatment of the cardiovascular system was often conducted by directly accessing the impacted part of the system. For example, treatment of a blockage in one or more of the coronary arteries was traditionally treated using coronary artery bypass surgery. As can be readily appreciated, such therapies are rather invasive to the patient and require significant recovery times and/or treatments. More recently, less invasive therapies have been developed, for example, where a blocked coronary artery could be accessed and treated via a percutaneous catheter (e.g., angioplasty). Such therapies have gained wide acceptance among patients and clinicians.

Some relatively common medical conditions may include or be the result of inefficiency, ineffectiveness, or complete failure of one or more of the valves within the heart. For example, failure of the aortic valve can have a serious effect on a human and could lead to serious health condition and/or death if not dealt with. Treatment of defective heart valves poses other challenges in that the treatment often requires the repair or outright replacement of the defective valve. Such therapies may be highly invasive to the patient. Disclosed herein are medical devices that may be used for delivering a medical device to a portion of the cardiovascular system in order to diagnose, treat, and/or repair the system. At least some of the medical devices disclosed herein may be used to deliver and implant a replacement heart valve (e.g., a replacement aortic valve). In addition, the devices disclosed herein may deliver the replacement heart valve percutaneously and, thus, may be much less invasive to the patient. The devices disclosed herein may also provide a number of additional desirable features and benefits as described in more detail below.

The figures illustrate selected components and/or arrangements of a medical device system 10. It should be noted that in any given figure, some features of the medical device system 10 may not be shown, or may be shown schematically, for simplicity. Additional details regarding some of the components of the medical device system 10 may be illustrated in other figures in greater detail. A medical device system 10 may be used to deliver and/or deploy a variety of medical devices to a number of locations within the anatomy. In at least some embodiments, the medical device system 10 may include a replacement heart valve delivery system (e.g., a replacement aortic valve delivery system) that can be used for percutaneous delivery of a replacement heart valve. This, however, is not intended to be limiting as the medical device system 10 may also be used for other interventions including mitral valve replacement, valve repair, valvuloplasty, and the like, or other similar interventions.

Figure 2:
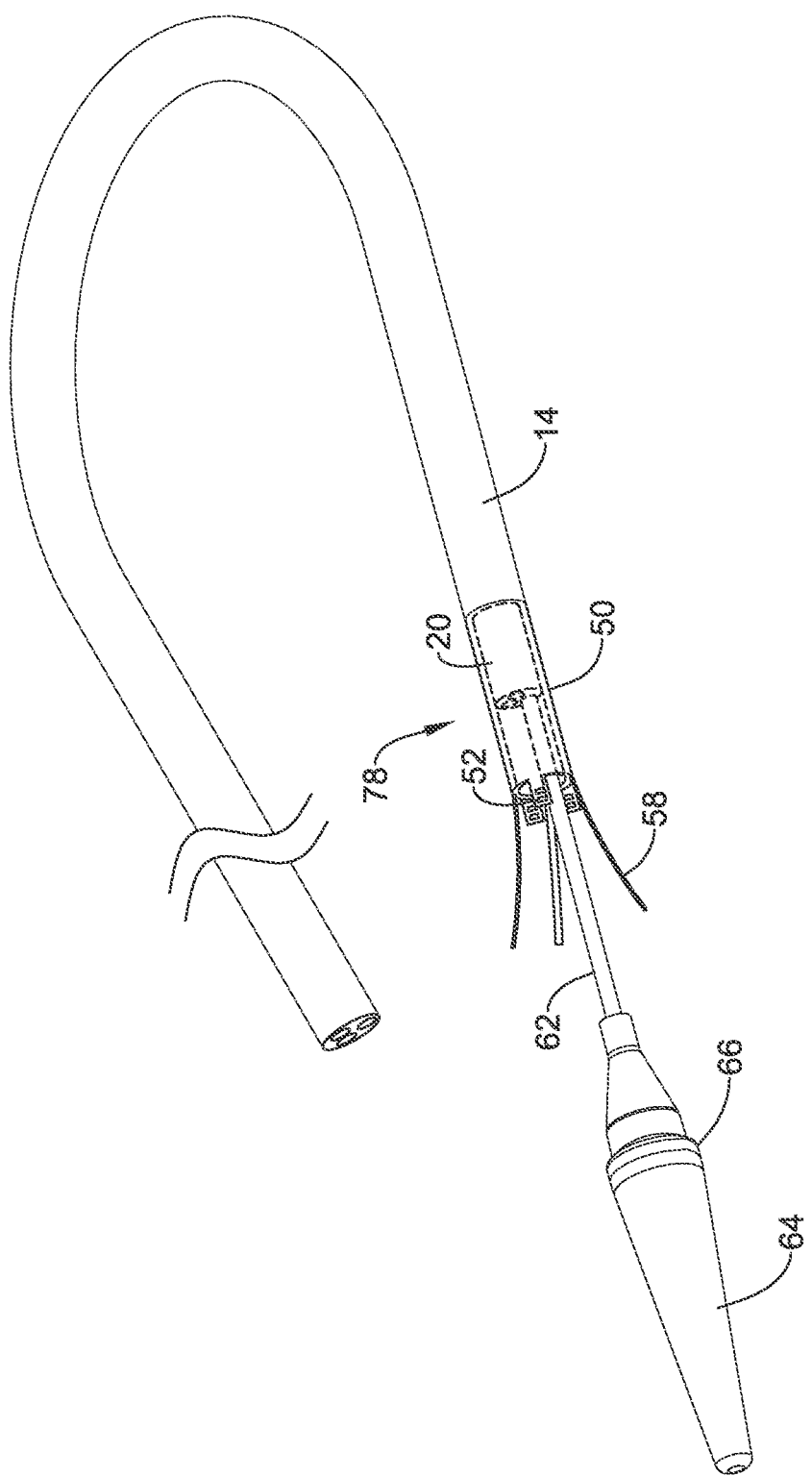
FIG. 2 illustrates a portion of the example medical device system of FIG. 1.

The medical device system 10, as seen in FIG. 1 for example, may generally be described as a catheter system that includes a delivery system having an outer sheath 12 for a medical implant 16 (i.e., a replacement valve implant, for example, which term may be used interchangeably with the term "medical implant" herein) which may be coupled to the delivery system and disposed within a lumen of the outer sheath 12 during delivery of the medical implant 16. In some embodiments, the delivery system may include an inner catheter 14, as seen in FIG. 2 for example, extending at least partially through the outer sheath 12 (partially seen in phantom in FIG. 1). In some embodiments, the medical implant 16 may be coupled to the inner catheter 14 and disposed within the lumen of the outer sheath 12 during delivery of the medical implant 16. In some embodiments, a handle 18 may be disposed and/or attached at a proximal end of the delivery system, as seen in FIG. 1, and may include one or more actuation means associated therewith. In some embodiments, the handle 18 may be configured to manipulate the position of the outer sheath 12 relative to the inner catheter 14, and/or aid in the deployment of the medical implant 16. In some embodiments, the medical device system 10 may include a nose cone 64 disposed at a distal end of a guidewire extension tube 62, wherein the guidewire extension tube 62 may extend distally from the inner catheter 14. In at least some embodiments, the nose cone 64 may be designed to have an atraumatic shape. In some embodiments, the nose cone 64 may include a ridge or ledge 66 that is configured to abut a distal tip of the outer sheath 12 during delivery of the medical implant 16.

Figure 3:
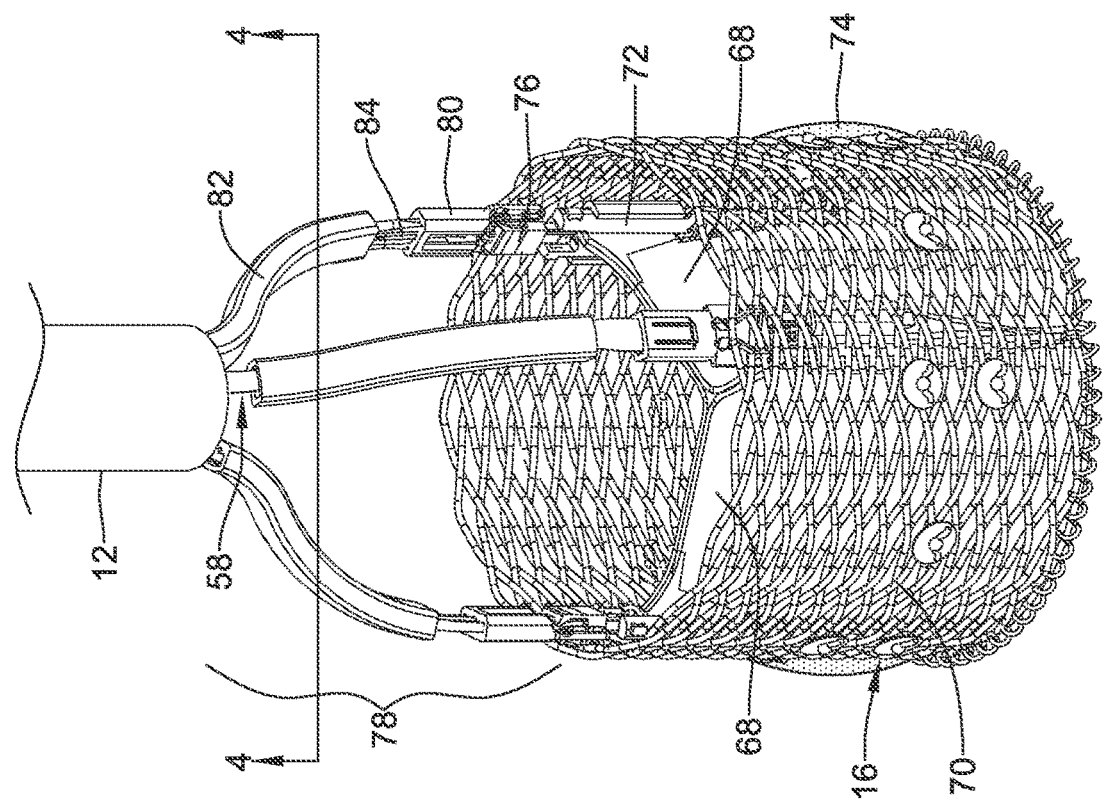
FIG. 3 illustrates an example medical implant associated with an example medical device system.

In use, the medical device system 10 may be advanced percutaneously through the vasculature to a position adjacent to an area of interest or a target location. For example, the medical device system 10 may be advanced through the vasculature and across the aortic arch to a position adjacent to a defective aortic valve. Alternative approaches to treat a defective aortic valve and/or other heart valve(s) are also contemplated with the medical device system 10. During delivery, the medical implant 16 may be generally disposed in an elongated and low profile "delivery" configuration within the delivery system and/or the outer sheath 12 coupled to and/or distal of the inner catheter 14. Once positioned, the outer sheath 12 may be retracted relative to the inner catheter 14, which may be held stationary by the handle 18, and/or the medical implant 16 to expose the medical implant 16. The medical implant 16 may be actuated using the handle 18 in order to translate the medical implant 16 into a generally expanded and larger profile "deployed" configuration suitable for implantation within the anatomy (as seen in FIG. 3, for example). When the medical implant 16 is suitably deployed within the anatomy, the medical implant 16 may be released and/or detached from the medical device system 10, the delivery system can be removed from the vasculature, leaving the medical implant 16 in place in a "released" configuration to function as, for example, a suitable replacement for the native aortic valve. In at least some interventions, the medical implant 16 may be deployed within the native valve (e.g., the native valve is left in place and not excised). Alternatively, the native valve may be removed (such as through valvuloplasty, for example) and the medical implant 16 may be deployed in its place as a replacement.

In some embodiments, the inner catheter 14 may include one or more lumens extending therethrough, as seen in FIG. 2 for example. For example, in some embodiments, the inner catheter 14 may include a first lumen, a second lumen, a third lumen, and a fourth lumen. Other configurations are also contemplated. In general, the one or more lumens extend along an entire length of the inner catheter 14. Other embodiments are contemplated, however, where one or more of the one or more lumens extend along only a portion of the length of the inner catheter 14. For example, in some embodiments, the fourth lumen may stop just short of a distal end of the inner catheter 14 and/or be filled in at its distal end to effectively end the fourth lumen proximal of the distal end of the inner catheter 14. In some embodiments, a distal region of the inner catheter 14 may include a step in outer diameter that defines a decreased diameter section 20. In some embodiments, the decreased diameter section 20 may define a region where other components of the medical device system 10 may be attached. For example, in some embodiments, a coupler assembly 78 (described further below) maybe attached to the inner catheter 14 at the decreased diameter section 20 and/or at a distal end of the inner catheter 14.

In some embodiments, the inner catheter 14 may include an extruded, multi-lumen polymeric shaft. Other forms are also contemplated including other polymer shafts or tubes, metallic shafts or tubes, reinforced shafts or tubes, or the like including other suitable materials such as those disclosed herein. In some embodiments, the inner catheter 14 may be a singular monolithic or unitary member. In some embodiments, the inner catheter 14 may include a plurality of portions or segments that are coupled together. The total length of the inner catheter 14 may be in the range of about 60 to 150 cm, or about 80 to 120 cm, or about 100 to 115 cm, or about 112±0.02 cm. In some embodiments, the inner catheter 14 may have one or more sections with a differing hardness/stiffness (e.g., differing shore durometer). For example, the inner catheter 14 may have a proximal region and an intermediate region. In some embodiments, the proximal region may include a generally stiff polymeric material such as a 72D polyether block amide (e.g., 72D PEBAX) and may have a length in the range of about 60 to 150 cm, or about 80 to 120 cm, or about 100 to 115 cm, or about 109.5±0.02 cm. In some embodiments, the intermediate region may include a 40D polyether block amide (e.g., 40D PEBAX) and may have a length in the range of about 5 to 25 mm, or about 10 to 20 mm, or about 15±0.01 mm.

The decreased outer diameter section may also differ from the proximal region and/or the intermediate region and, in some embodiments, may include a 72D polyether block amide (e.g., 72D PEBAX) and may have a length in the range of about 0.5 to 2 cm (5 to 20 mm), or about 0.8 to 1.5 cm (8 to 15 mm), or about 1±0.001 cm (10±0.01 mm). These are just examples.

In some embodiments, disposed within one of the lumens (e.g., a first lumen) of the inner catheter 14 may be at least one actuator element 84, which may be used to actuate (i.e., translate axially or longitudinally, and/or expand) the medical implant 16 between a delivery configuration and a deployed configuration. In some cases, the actuator element(s) 84 may herein be referred to, or used interchangeably with, the term "actuator element". In some embodiments, the medical device system 10 may include at least one actuator element 84. In some embodiments, the at least one actuator element 84 may include a plurality of actuator elements 84, two actuator elements 84, three actuator elements 84, four actuator elements 84, or another suitable or desired number of actuator elements 84. For the purpose of illustration only, the medical device system 10 and/or the medical implant 16 is shown with three actuator elements 84.

In at least some embodiments, the first lumen may be lined with a low friction liner (e.g., a FEP liner). In some embodiments, disposed within a second lumen may be at least one release pin, although dedicated release pins are not strictly necessary in every embodiment. In at least some embodiments, the second lumen may be lined with a hypotube liner. A third lumen may be a guidewire lumen and in some embodiments, the third lumen may also be lined with a hypotube liner. In some embodiments, a fourth lumen may be used to house a non-stretch wire or other reinforcing member. The form of the non-stretch wire or other reinforcing member may vary. In some embodiments, the non-stretch wire may take the form of a stainless steel braid. The non-stretch wire may optionally include a pair of longitudinally-extending aramid and/or para aramid strands (for example, KEVLAR®) disposed on opposite sides of the braid. In general, rather than being "disposed within" the fourth lumen, the non-stretch wire may be embedded within the fourth lumen. In addition, the non-stretch wire may extend to a position adjacent to a distal end region but not fully to the distal end of the inner catheter 14. For example, a short distal segment of the fourth lumen may be filled in with polymer material adjacent to the distal end of the inner catheter 14.

It is to be noted that in order to facilitate understanding, certain features of the disclosure may be described in the singular, even though those features may be plural or recurring within the disclosed embodiment(s). Each instance of the features may include and/or be encompassed by the singular disclosure(s), unless expressly stated to the contrary. For example, a reference to "the actuator element", "the locking element", "the lumen", or other features may be equally referred to all instances and quantities beyond one of said feature. As such, it will be understood that the following discussion may apply equally to any and/or all of the components for which there are more than one within the medical implant 16 (i.e., the at least one actuator element 84, the plurality of locking elements 76, the plurality of fingers 58, etc.) and/or the medical device system 10, unless explicitly stated to the contrary. Additionally, not all instances of some elements or features may be shown in each figure for clarity.

FIG. 3 illustrates some selected components of the medical device system 10 and/or the medical implant 16. For example, here it can be seen that the medical implant 16 may include a plurality of valve leaflets 68 (e.g., bovine pericardial, polymeric, etc.) which may be secured to a braided anchor member 70 that is reversibly actuatable between an elongated "delivery" configuration, and an expanded "deployed" configuration. In some embodiments, the braided anchor member 70 may form a tubular structure defining a central longitudinal axis. In some embodiments, the medical implant 16 may include a plurality of locking elements 76 attached to the braided anchor member 70, the plurality of locking elements 76 being configured to lock the braided anchor member 70 in the "deployed" and/or "released" configuration(s). In some embodiments, at least one actuator element 84 may be configured to actuate the braided anchor member 70 and/or the medical implant 16 between the "delivery" configuration and the "deployed" configuration and/or the "released" configuration.

In some embodiments, the plurality of locking elements 76 may each comprise a post member, for example at the commissure portions of the valve leaflets 68 (the post member may sometimes be referred to as a portion of a commissure post, which may serve to secure the valve leaflets 68, or the post member may be connected and/or attached to a commissure post), and a buckle member or other receiving element configured to slidably receive the post member therein. In other words, in at least some embodiments, a medical implant 16 may include a plurality of post members and a corresponding a plurality of buckle members. Other configurations and correspondences are also contemplated. In some embodiments, the valve leaflets 68 may also be secured to a base or distal end of the braided anchor member 70. The post members and/or the commissure posts, in turn, may be secured and/or attached to the braided anchor member 70 (e.g., along the interior of the braided anchor member) with sutures, adhesives, or other suitable mechanisms. In some embodiments, the commissure post and/or the post member may include one or more holes or other features provided to aid in securing and/or attaching the commissure post and/or the post member to the braided anchor member 70. Positioned adjacent to (e.g., aligned with) the plurality of post members are a corresponding plurality of buckle members, which may be secured and/or fixedly attached to the braided anchor member 70 (e.g., along the interior of the braided anchor member 70) with sutures, adhesives, or other suitable mechanisms. In some embodiments, the post member may be axially translatable relative to the buckle member generally parallel to the central longitudinal axis of the braided anchor member 70 when the post member is at least partially disposed within and/or engaged with the buckle member.

In some embodiments, one buckle member may be fixedly attached to the braided anchor member 70 adjacent to each of the three post members. Accordingly, in some embodiments, the braided anchor member 70 may have a total of three buckle members and three post members attached thereto. Similarly, one actuator element 84 may be associated with each post member and buckle member, for a total of three actuator elements 84 in the illustrated example(s). Other embodiments are contemplated where fewer or more buckle members, post members, and/or actuator elements 84 may be utilized. In some embodiments, a seal 74 (shown in partial cross-section in FIG. 3) may be disposed on and/or about the braided anchor member 70 and may help to seal the medical implant 16 within a target site or area of interest upon deployment.

In at least some embodiments, the buckle member may be configured to slidably receive at least a portion of the post member within the longitudinal channel. In some embodiments, the buckle member may include one or more holes or other features provided to aid in attaching the buckle member to the braided anchor member 70. In some embodiments, the buckle member may be configured to engage with and/or lock the post member in the "deployed" configuration, such that distal axial translation of the post member relative to the buckle member is prevented. Some suitable but non-limiting materials for the buckle member and/or the post member, for example metallic materials or polymeric materials, may be described below.

In some embodiments, attachment between the medical implant 16 and the inner catheter 14 and/or the delivery system may be effected through the use of a coupler assembly 78, as seen in FIGS. 2-3 for example. In at least some embodiments, the coupler assembly 78 may generally include a coupler ring 50 disposed about and/or fixedly attached to the decreased diameter section 20 and/or at a distal end of the inner catheter 14. In some embodiments, the coupler assembly 78 may include a plurality of fingers 58 extending distally from the coupler ring 50. In some embodiments, each of the plurality of fingers 58 may be releasably coupled to one locking element 76 of the medical implant 16. As such, the medical implant 16 may include a plurality of locking elements 76 corresponding to the plurality of fingers 58. A collar 80 may further assist in holding together these structures. A guide 82 may be disposed over each of the fingers 58 and may serve to keep the plurality of fingers 58 of the coupler assembly 78 associated with the at least one actuator element 84 extending adjacent to the coupler assembly 78.

In some embodiments, an example actuator element 84 may include a proximal end and a distal end. In use, the proximal end may be connected to the handle 18, and/or manipulated or otherwise actuated by a user using the handle 18, to shift the braided anchor member 70 and/or the medical implant 16 from a "delivery" configuration to a "deployed" configuration, and later to a "released" configuration. In some embodiments, the actuator element 84 may include an elongated rod and a distal end portion. In some embodiments, the actuator element 84 and/or the distal end portion may be releasably connected to and/or coupled to the locking element 76. In some embodiments, the distal end portion may be integrally formed with or as a part of the elongated rod as a single monolithic structure. In some embodiments, the actuator element 84 may be prevented from rotating (i.e., is non-rotatable) relative to the locking element 76 when the actuator element 84 is engaged with the locking element 76. In some embodiments, after shifting the braided anchor member 70 and/or the medical implant 16 from the "delivery" configuration to the "deployed" configuration, continued proximal retraction, withdrawal, and/or translation of the at least one actuator element 84 may shift the braided anchor member 70 and/or the medical implant 16 from the "deployed" configuration to the "released" configuration. When shifting the braided anchor member 70 and/or the medical implant 16 from the "deployed" configuration to the "released" configuration, the distal end portion of the at least one actuator element 84 may engage with the collar 80, thereby retracting, withdrawing, and/or translating proximally the collar 80 relative to the locking element 76 to release the braided anchor member 70 and/or the medical implant 16.

In some embodiments, the actuator element 84 and/or the elongated rod may be generally round, oblong, ovoid, rectangular, polygonal (i.e., two-sided, three-sided, four-sided, five-sided, six-sided, etc.) and/or combinations thereof in shape. Other shapes, both regular and irregular, are also contemplated. In some embodiments, the actuator element 84 may be formed from a single piece of wire, round stock, or other suitable material, as discussed herein. In some embodiments, the actuator element 84 may be formed by further processing the single piece of wire, round stock, or other suitable material, such as by machining, stamping, laser cutting, etc. Some suitable but non-limiting materials for the actuator element 84, the elongated rod, and/or the distal end portion, for example metallic materials or polymeric materials, may be described below.

Figure 4:
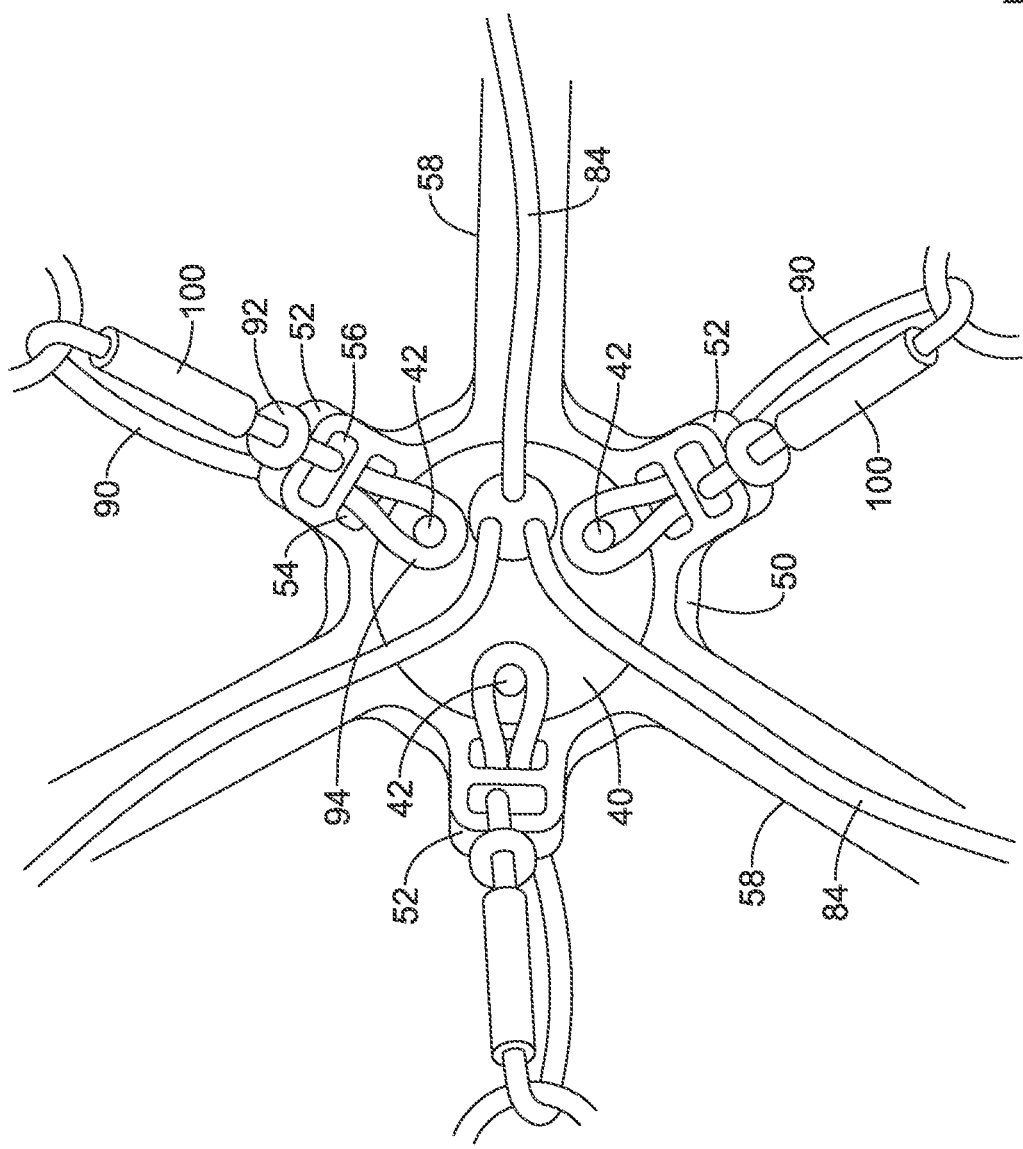
FIG. 4 illustrates a modified end view of a portion of an example medical device system taken along line 4-4 in FIG. 3.
Figure 5:
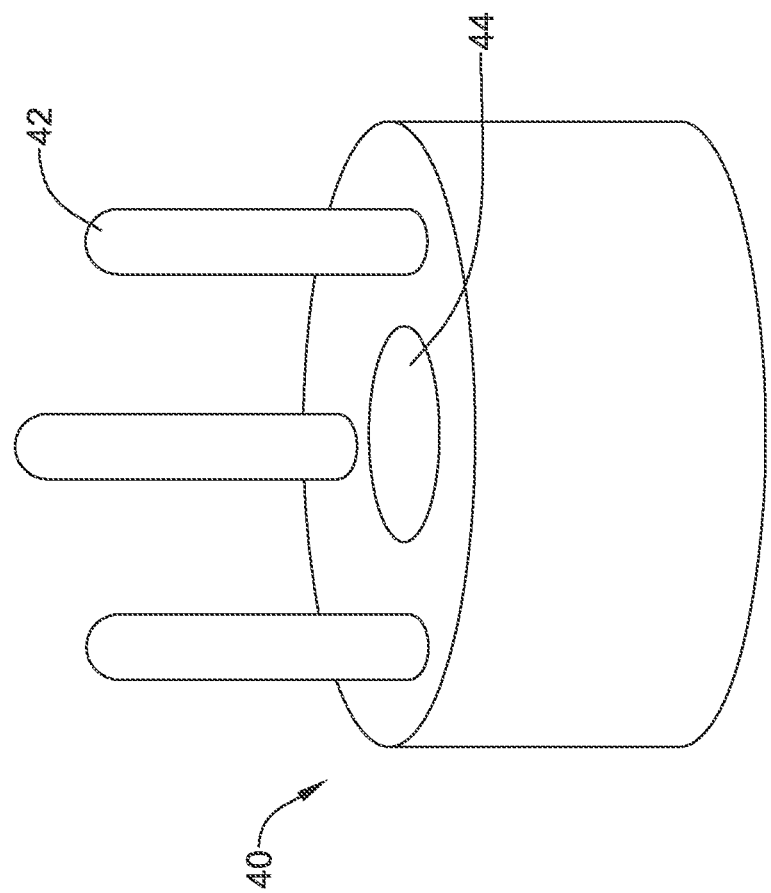
FIG. 5 illustrates an example cleat disc of an example medical device system.

As seen in greater detail in FIG. 4, which shows a modified, partially splayed-out end view of the distal end of the inner catheter 14, in some embodiments, the coupler assembly 78 may include one or more suture anchors 52 extending distally from the coupler ring 50, each suture anchor 52 including a proximal aperture 54 extending laterally and/or radially therethrough, and a distal aperture 56 extending laterally and/or radially therethrough relative to a central longitudinal axis of the inner catheter 14. In some embodiments, the proximal aperture 54 may be distinct and/or separate from the distal aperture 56. Also visible in FIG. 4 is a cleat disc 40 (e.g., a release mechanism, a release element, etc., which terms may be used interchangeably with a cleat disc herein), which may be disposed distal of the inner catheter 14 and/or within the coupler assembly 78. In at least some embodiments, the cleat disc 40 may be at least partially disposed within a lumen of the coupler ring 50. In some embodiments, the cleat disc 40 may include one or more cleat posts 42 (e.g., one or more release pins, one or more protrusions, etc., which terms may be used interchangeably with one or more cleats herein) extending distally therefrom, as seen in FIGS. 4-5 for example. In some embodiments, the one or more cleat posts 42 may comprise two cleats, three cleats, four cleats, or another suitable number of cleats. In some embodiments, the one or more cleat posts 42 may be fixedly attached to the cleat disc 40. In some embodiments, the one or more cleat posts 42 may be integrally formed with the cleat disc 40 as a single unitary structure. In some embodiments, the cleat disc 40 may include an actuator lumen 44 extending therethrough. In at least some embodiments, the at least one actuator element 84 may extend through the actuator lumen 44 of the cleat disc 40.

In some embodiments, a sheathing aid 200 may extend between and/or connect the delivery system to the medical implant 16. In some embodiments, the sheathing aid 200 may be configured to guide the medical implant 16 into the outer sheath 12 upon relative closing movement therebetween, as will be described in more detail below. In some embodiments, the sheathing aid 200 may include a plurality of filaments 90 (e.g., a plurality of tethers, a plurality of tensioning elements, a plurality of sutures, etc., which terms may be used interchangeably with a plurality of filaments herein) extending distally from the inner catheter 14 and/or one suture anchor 52 to a proximal end of the braided anchor member 70 of the medical implant 16. In at least some embodiments, the plurality of filaments 90 may be releasably coupled to the cleat disc 40 and/or the one or more cleat posts 42.

Figure 6:
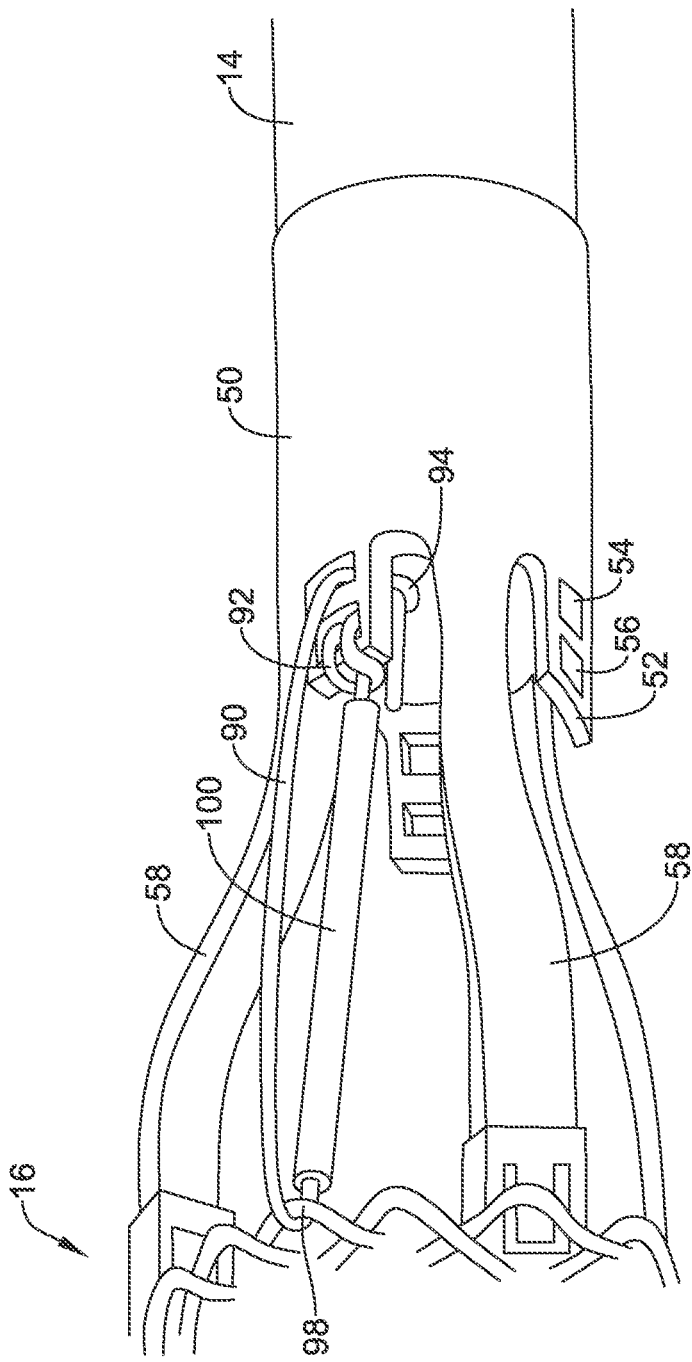
FIG. 6 illustrates selected components of an example medical device system.

Also illustrated in FIGS. 4 and 6 is one of a plurality of filaments 90 extending distally from the inner catheter 14 and/or one suture anchor 52 to a proximal end of the braided anchor member 70 of the medical implant 16. In some embodiments, each of the plurality of filaments 90 may include a first end having a first end loop 92 and a second end having a second end loop 94. In some embodiments, each of the plurality of filaments 90 may include a filament body extending between the first end and the second end, the filament body having a tubular member 100 (e.g., a thin-walled hypotube, etc.) disposed thereon. The first end loop 92 may extend through the distal aperture 56 and toward a distalmost end of the suture anchor 52, where the filament body may pass through the first end loop 92, thereby securing the first end of the filament 90 to the suture anchor 52. The filament body may then extend distally toward the proximal end of the braided anchor member 70 of the medical implant 16, where the filament body extends through and/or loops around a crown 98 of the braided anchor member 70. The filament body then extends back proximally toward the suture anchor 52, wherein the second end loop 94 extends through the proximal aperture 54 and into or within the lumen of the coupler ring 50. At a location within the coupler ring 50, the second end loop 94 extends over and/or around one of the one or more cleat posts 42 to releasably coupling the filament 90 to the cleat disc 40, the suture anchor 52, the coupler ring 50, and/or the coupler assembly 78.

Figure 7:
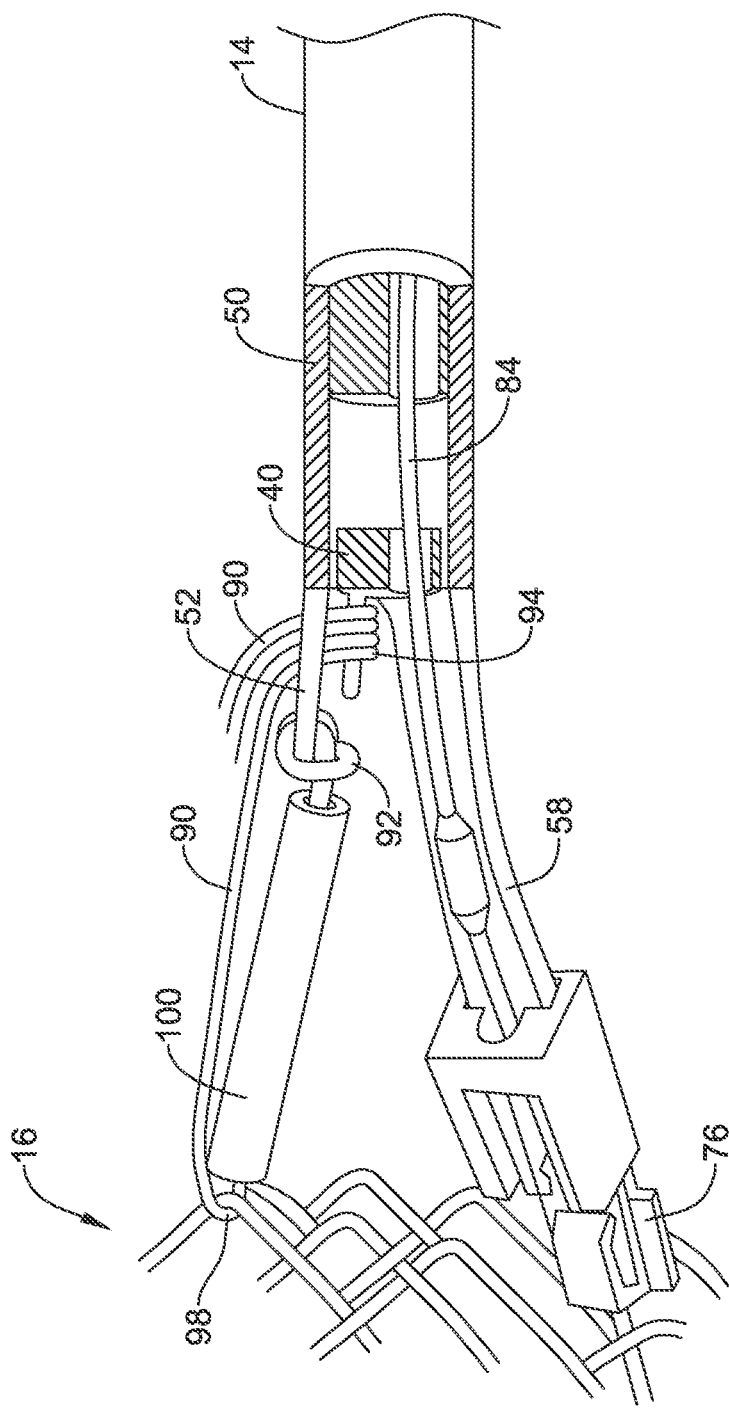
FIG. 7 illustrates a partial cut-away view of selected components of an example medical device system in a deployed configuration.

In other words, one of the one or more cleat posts 42 extends through the second end loop 94 when the cleat disc 40 is disposed at a distal position within the lumen of the coupler ring 50 to releasably couple the filament 90 thereto, as seen in FIG. 7 for example. In the distal position, the one or more cleat posts 42 extend distally past the proximal aperture 54 such that the second end loop(s) 94 cannot be removed from the cleat post(s) 42 and/or pulled through the proximal aperture 54. The skilled person will recognize that, if desired, the arrangement of the end loops through the apertures may be reversed within the scope of this disclosure such that the second end loop 94 extends through the distal aperture 56 and the first end loop 92 extends through the proximal aperture 54. Other configurations are also contemplated.

As will become apparent from the discussion below and other figures associated with the disclosure, in some embodiments, one of the plurality of filaments 90 may extend between each crown 98 of the braided anchor member 70 and the distal end of the inner catheter 14, the coupler ring 50, the coupler assembly 78, and/or the suture anchor 52. In some embodiments, more than one of the plurality of filaments 90 may be coupled to each cleat post 42, as seen illustratively in FIG. 7 for example. In some embodiments, two of the plurality of filaments 90 may be coupled to each cleat post 42, three of the plurality of filaments 90 may be coupled to each cleat post 42, four of the plurality of filaments 90 may be coupled to each cleat post 42, five of the plurality of filaments 90 may be coupled to each cleat post 42, six of the plurality of filaments 90 may be coupled to each cleat post 42, etc.

In some embodiments, each filament 90 of the plurality of filaments 90 extending through and/or looping around a crown 98 of the braided anchor member 70 disposed between adjacent fingers 58 may extend to one suture anchor 52 (e.g., the same suture anchor 52) that is also disposed between the same adjacent fingers 58 and may be secured to one cleat post 42 (e.g., the same cleat post 42). In general, the medical device system 10 may include one filament 90 (e.g., only one filament 90, exactly one filament 90, a single filament 90, etc.) of the plurality of filaments 90 extending through and/or looping around any given crown 98 of the braided anchor member 70, although other configurations are contemplated. In some embodiments, not all crowns 98 of the braided anchor member 70 include a filament 90 of the plurality of filaments 90 extending through and/or looping around them. In other words, in some embodiments, some of the crowns 98 (e.g., some quantity less than all) may include a filament 90 of the plurality of filaments 90 extending through and/or looping around them.

Figure 8:
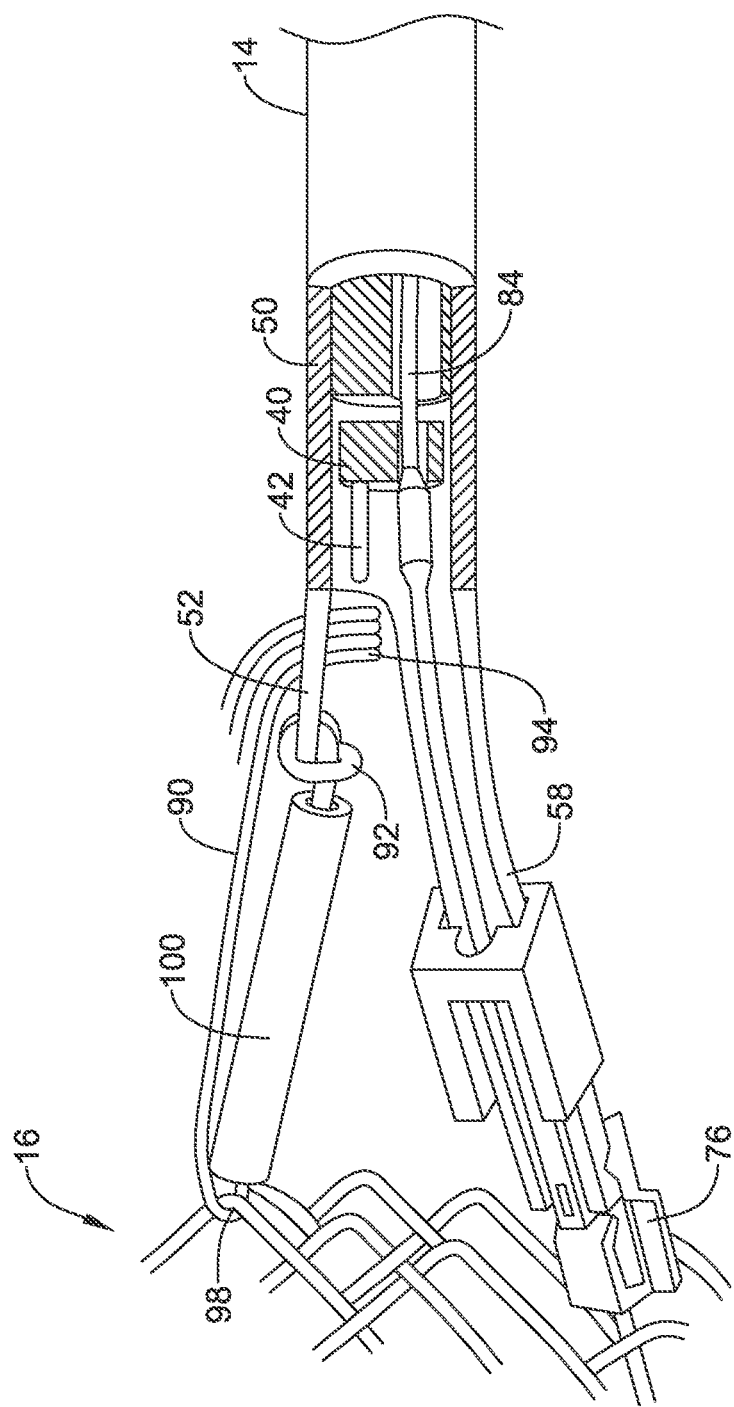
FIG. 8 illustrates a partial cut-away view of selected components of an example medical device system in a partially-released configuration.
Figure 9:
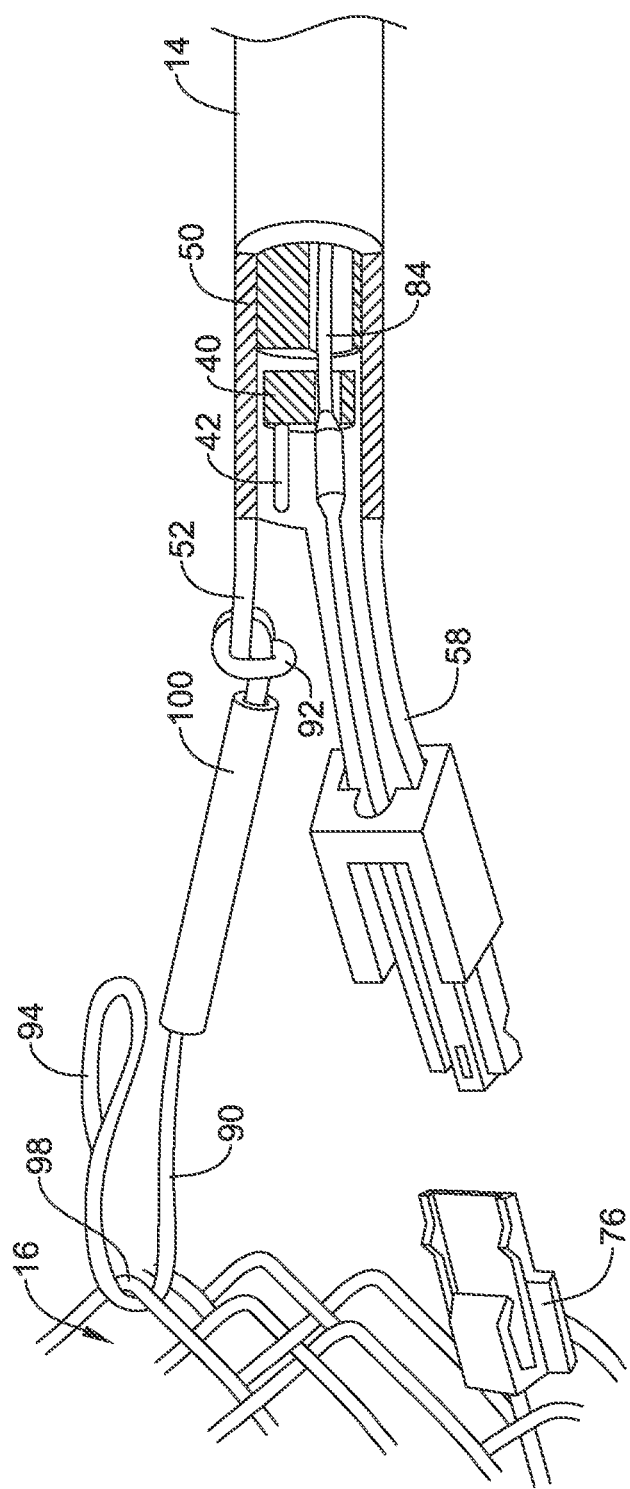
FIG. 9 illustrates a partial cut-away view of selected components of an example medical device system in a released configuration.

In some embodiments, the at least one actuator element 84 may include an enlarged portion and/or an additional structural feature (e.g., a tubular sleeve, etc.) disposed thereon distal of the cleat disc 40 and proximal to a distal end of the at least one actuator element 84, as will be described in more detail below with reference to FIGS. 10-12. During the release process for the medical implant 16, (e.g., as the medical implant 16 is actuated from the "delivery" configuration to the "deployed" configuration to the "released" configuration), the at least one actuator element 84 may be retracted, withdrawn, and/or translated proximally relative to the inner catheter 14, the medical implant 16, and/or the braided anchor member 70. As the at least one actuator element 84 is retracted, withdrawn, and/or translated proximally, the enlarged portion and/or the additional structural feature (e.g., a tubular sleeve, etc.) may contact the cleat disc 40 when the cleat disc 40 is in the distal position, wherein continued retraction, withdrawal, and/or proximal translation of the at least one actuator element 84 may pull, slide, and/or translate the cleat disc 40 proximally within the lumen of the coupler ring 50 toward a proximal position, as seen in FIG. 8 for example, to release the plurality of filaments 90 from the one or more cleat posts 42. In some embodiments, proximal retraction and/or translation of the cleat disc 40 to the proximal position may move and/or translate the one or more cleat posts 42 such that the one or more cleat posts 42 no longer extend distally past the proximal aperture 54, thereby allowing the second end loop(s) 94 to be removed from the cleat post(s) 42 and/or allowing the second end loop(s) 94 to be pulled through the proximal aperture 54, as seen in FIG. 9 for example. In some embodiments, proximal retraction and/or translation of the cleat disc 40 to the proximal position may move and/or translate the one or more cleat posts 42 such that the one or more cleat posts 42 are pulled proximally through and/or are removed from the second end loop(s) 94, thereby allowing the second end loop(s) 94 to be pulled through the proximal aperture 54, as seen in FIG. 9 for example.

Once the cleat disc 40 has been pulled to the proximal position and/or the second end loop(s) 94 is pulled through the proximal aperture 54, continued proximal retraction, withdrawal, and/or proximal translation of the at least one actuator element 84 may pull the plurality of filaments 90 through the crowns 98 of the braided anchor member 70 and pull the plurality of fingers 58 away from the corresponding plurality of locking elements 76 to complete the transition of the medical implant 16 from the "deployed" configuration to the "released" configuration. The inner catheter 14 and/or the coupler assembly 78 may be re-sheathed within the outer sheath 12 via relative translation therebetween (e.g., advancing the outer sheath 12 distally over the inner catheter 14 and/or the coupler assembly 78, withdrawing the inner catheter 14 and/or the coupler assembly 78 proximally within the outer sheath 12, a combination thereof, etc.). Thereafter, the delivery system may be withdrawn and/or removed from the anatomy, leaving behind the expanded and deployed medical implant 16 disposed at the target site in a "released" configuration.

Figure 10:
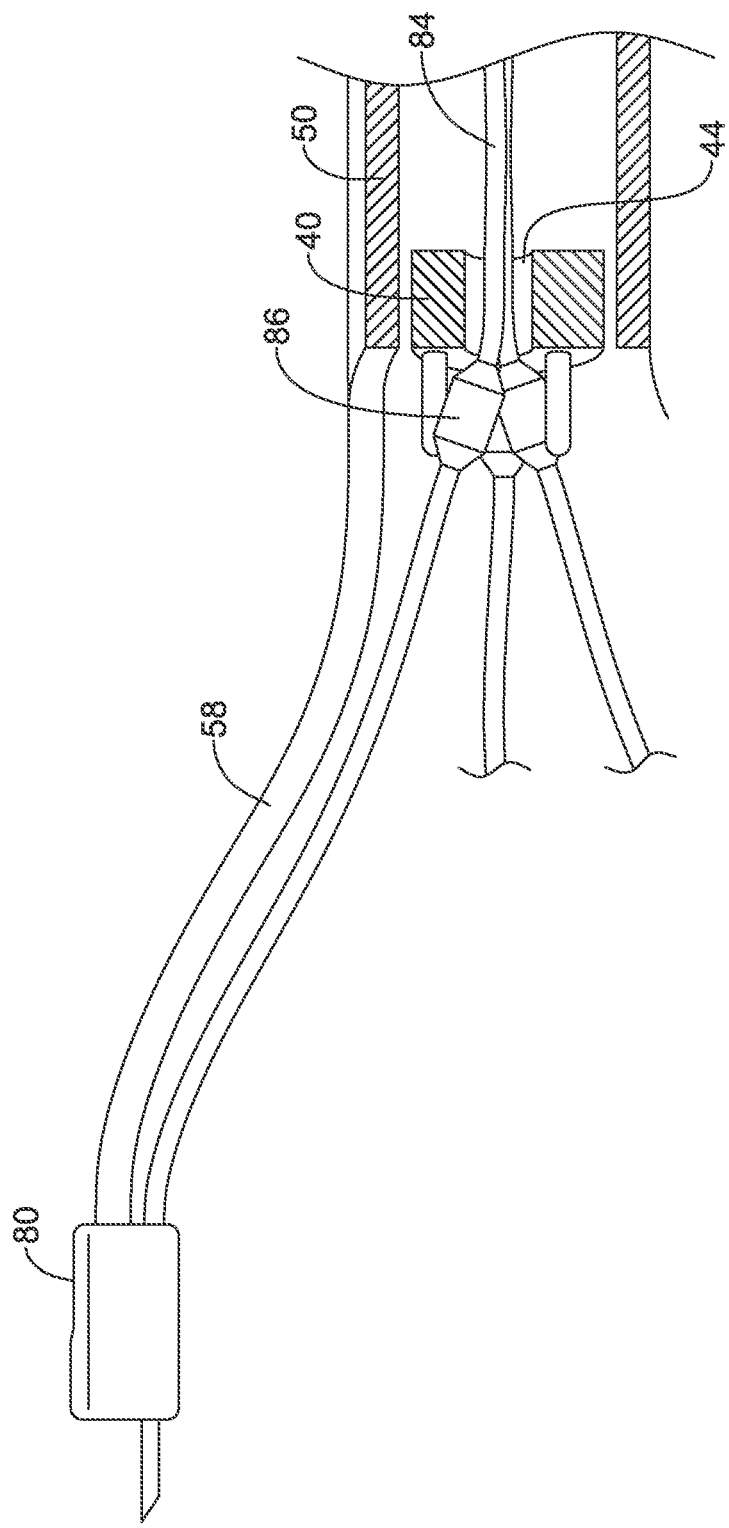
FIGS. 10-12 illustrate example actuation means associated with an example medical device system.
Figure 11:
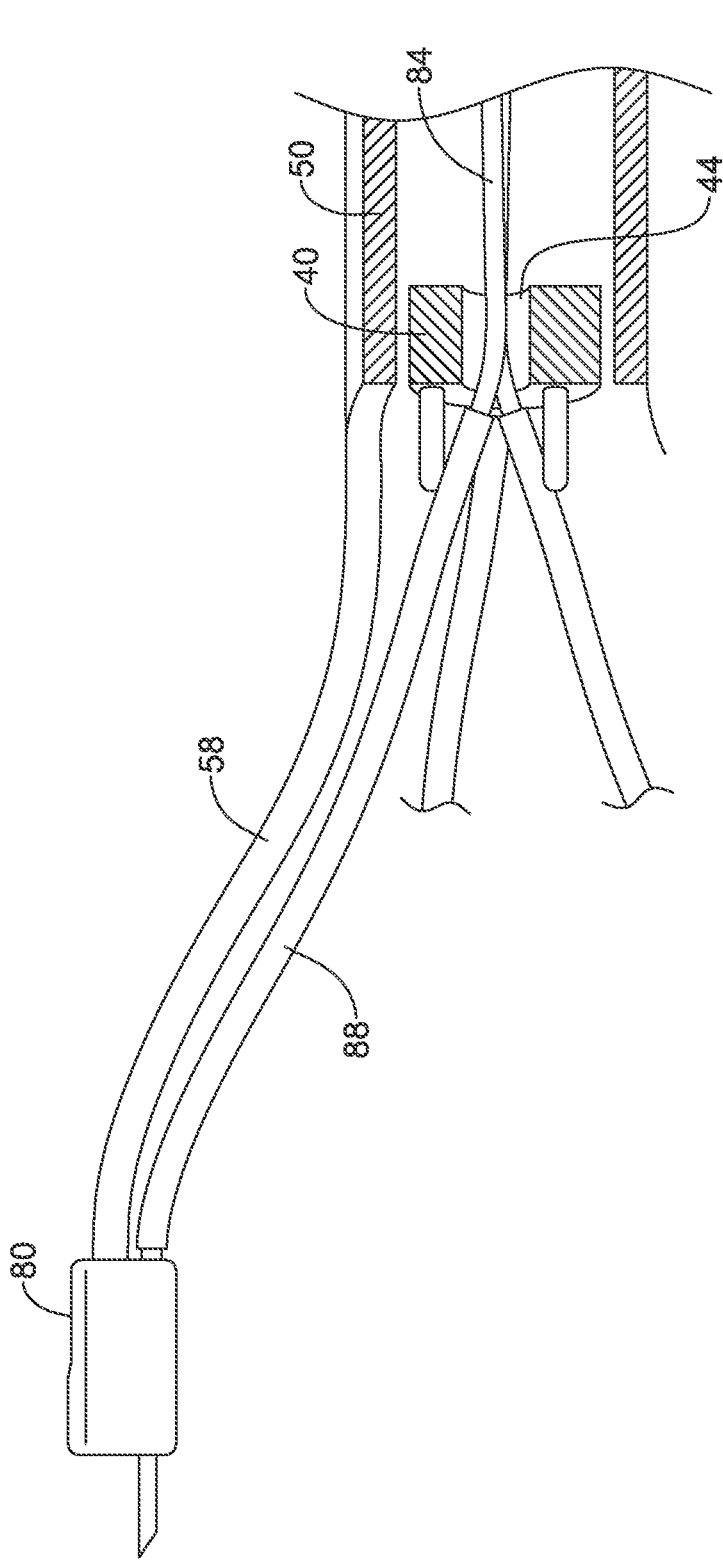
Figure 12:
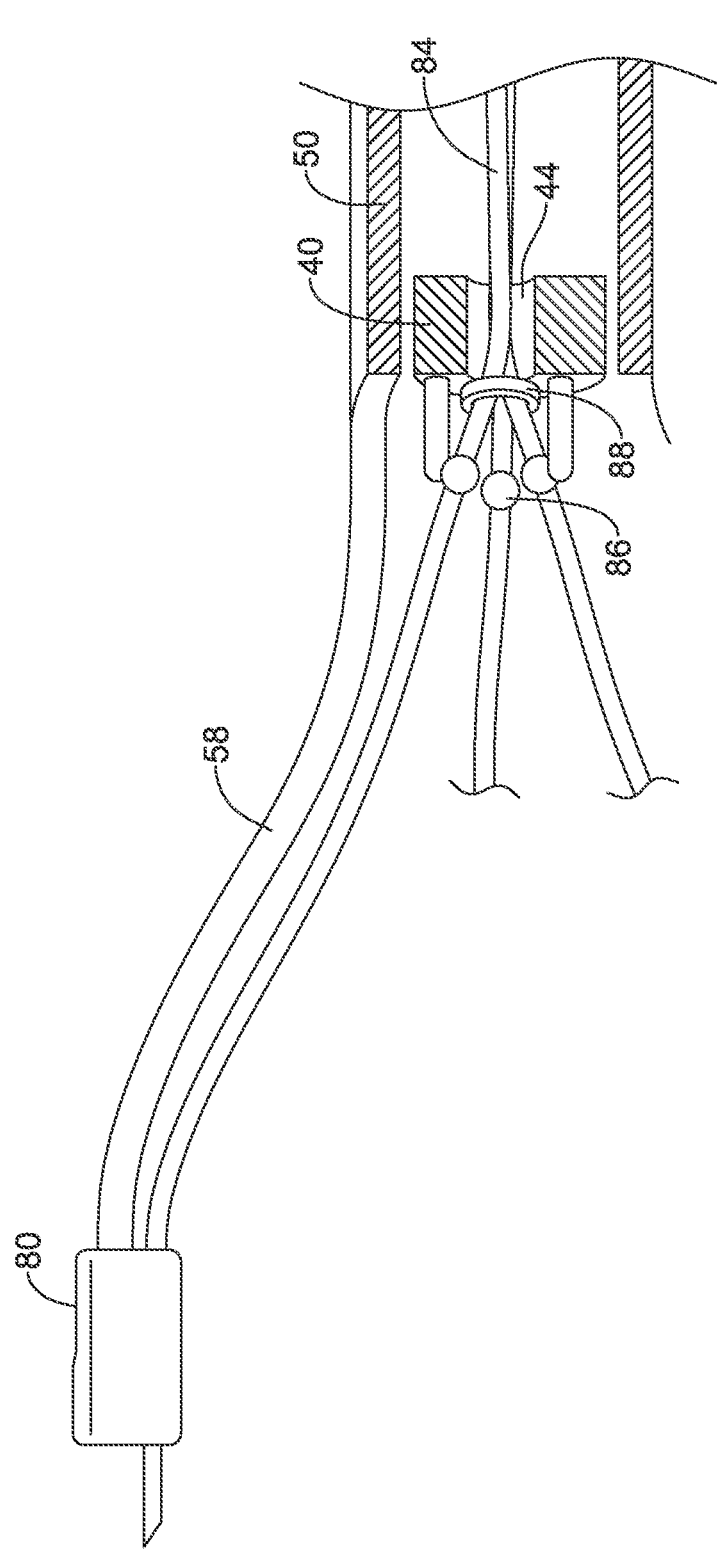

FIGS. 10-12 illustrate example configurations for the at least one actuator element 84, wherein the each of the at least one actuator element 84 may include an enlarged portion 86 (e.g., a ferrule, a protrusion, a stop element, etc.) and/or a tubular sleeve 88 disposed over the at least one actuator element 84. In at least some embodiments, the enlarged portion 86 and/or the tubular sleeve 88 have an outer diameter greater than an outer diameter of the at least one actuator element 84. It is noted that FIGS. 10-12 illustrate a single complete actuator element 84, and only selected portions of other features for clarity and ease of understanding. In some embodiments, the enlarged portion 86 and/or the tubular sleeve 88 may be disposed distal of the cleat disc 40 and may be disposed proximal of the plurality of locking elements 76 and/or the collar 80. In other words, the enlarged portion 86 and/or the tubular sleeve 88 may be disposed between the cleat disc 40 and the medical implant 16.

Upon deployment of the medical implant 16, proximal retraction, withdrawal, and/or proximal translation of the at least one actuator element 84 through the actuator lumen 44 of the cleat disc 40 may engage the enlarged portion 86 and/or the tubular sleeve 88 against a distal face of the cleat disc 40 in the distal position. In some embodiments, as seen in FIG. 10 for example, the enlarged portion 86 of each of the at least one actuator element 84, when combined, form an outer diameter and/or cross-sectional area that is greater than a diameter of the actuator lumen 44 of the cleat disc 40. As such, the combined enlarged portions 86 cannot be pulled, withdrawn, and/or translated through the cleat disc 40.

In some embodiments, as seen in FIG. 11 for example, each of the at least one actuator element 84 may include a tubular sleeve 88 disposed thereon. Proximal retraction, withdrawal, and/or proximal translation of the at least one actuator element 84 causes the collar 80 to also retract, withdraw, and/or translate proximally. As the collar 80 moves proximally, a proximal end of the collar 80 engages a distal end of the tubular sleeve 88 causing a proximal end of the tubular sleeve 88 to retract, withdraw, and/or translate proximally into engagement and/or contact with the distal face of the cleat disc 40 in the distal position. When combined, the tubular sleeve 88 of each of the at least one actuator element 84 forms an outer diameter and/or cross-sectional area that is greater than the diameter of the actuator lumen 44 of the cleat disc 40. As such, the combined tubular sleeves 88 cannot be pulled, withdrawn, and/or translated through the cleat disc 40.

In some embodiments, as seen in FIG. 12 for example, each of the at least one actuator element 84 may include an enlarged portion 86 disposed thereon, and a tubular sleeve 88 may be disposed about all of the at least one actuator element 84 such that all of the at least one actuator element 84 pass through the tubular sleeve 88. In this way, the tubular sleeve 88 has an outer diameter and/or cross-section greater than the diameter of the actuator lumen 44 of the cleat disc 40, and the enlarged portion 86 of each of the at least one actuator element 84, when combined, form an outer diameter and/or cross-sectional area that is greater than an inner diameter of the tubular sleeve 88. As such, the combined enlarged portions 86 cannot be pulled, withdrawn, and/or translated through the tubular sleeve 88. When the at least one actuator element 84 is retracted proximally, withdrawn, and/or translated proximally, the enlarged portion 86 engages a distal end of the tubular sleeve 88 and a proximal end of the tubular sleeve 88 engages the distal face of the cleat disc 40.

In each of the examples shown in FIGS. 10-12, further proximal retraction, withdrawal, and/or proximal translation of the at least one actuator element 84 may move the cleat disc 40 proximally toward the proximal position after the braided anchor member 70 and/or the medical implant 16 has been shifted to the "deployed" configuration, and/or as the braided anchor member 70 and/or the medical implant 16 is actuated and/or shifted from the "deployed" configuration to the "released" configuration.

Figure 13:
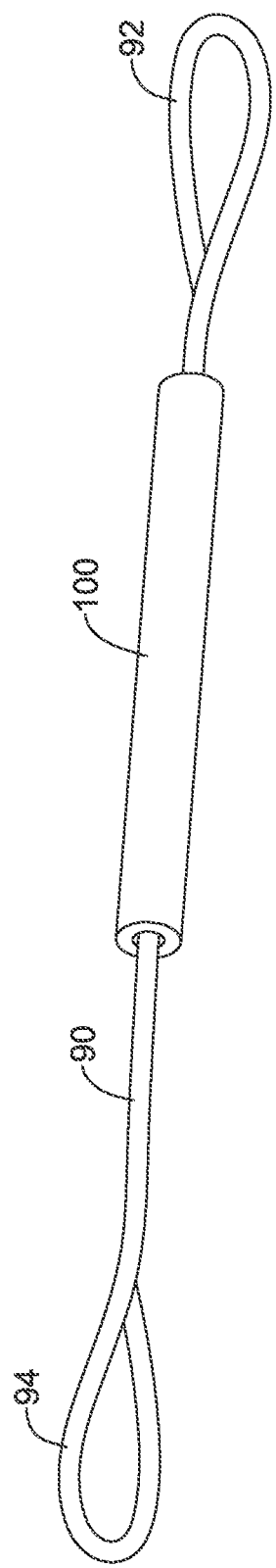
FIG. 13 illustrates selected components associated with an example medical device system.

FIG. 13 illustrates an example filament 90 having a tubular member 100 disposed thereon. The filament 90 may include a first end having first end loop 92 and a second end having a second end loop 94, as described above. In some embodiments, a filament body of the filament 90 extending between the first end loop 92 and the second end loop 94 may be longer than the tubular member 100 to facilitate extending the filament 90 back to the suture anchor 52 from the crown 98 of the braided anchor member 70. In some embodiments, the filament body of the filament 90 extending between the first end loop 92 and the second end loop 94 may be 25-100% longer than the tubular member 100 to facilitate extending the filament 90 back to the suture anchor 52 from the crown 98 of the braided anchor member 70. In some embodiments, the filament body of the filament 90 extending between the first end loop 92 and the second end loop 94 may be 50-100% longer than the tubular member 100 to facilitate extending the filament 90 back to the suture anchor 52 from the crown 98 of the braided anchor member 70. In some embodiments, the filament body of the filament 90 extending between the first end loop 92 and the second end loop 94 may be more than 100% longer than the tubular member 100 to facilitate extending the filament 90 back to the suture anchor 52 from the crown 98 of the braided anchor member 70.

As mentioned above, in some embodiments, the medical device system 10 may include a sheathing aid 200 extending between and/or connecting the delivery system, the inner catheter 14, and/or the coupler ring 50 to the medical implant 16. In some embodiments, the sheathing aid 200 may be configured to guide the medical implant 16 into the outer sheath 12 upon relative closing movement therebetween. The medical device system 10, through the use of the various components thereof, may be configured to allow a user (e.g., clinician, etc.) to "sheath", "unsheath", and "resheath" the medical implant 16. In other words, a user may manipulate the medical device system 10 so that the medical implant 16 shifts from an unsheathed configuration where the medical implant 16 is positioned generally outside of the outer sheath 12 to a sheathed or "delivery" configuration where the medical implant 16 is positioned within the outer sheath 12 (e.g., the user can "sheath" the medical implant 16). In addition, a user can also manipulate the medical device system 10 so that the medical implant 16 can shift from the sheathed or "delivery" configuration to an unsheathed or "deployed" configuration (e.g., the user can "unsheath" or "deploy" the medical implant 16). Moreover, the user can manipulate the medical device system 10 so that the medical implant 16 can again shift from the unsheathed or "deployed" configuration back to the sheathed or "delivery" configuration (e.g., the user can "resheath" the medical implant 16).

Because of the relatively compact nature of the medical device system 10 and the tendency for portions of the medical device system 10 (e.g., the medical implant 16) to be biased radially outward, the sheathing/unsheathing/resheathing processes may exert forces on, for example, the outer sheath 12. In addition, the configuration of the braided anchor member 70 may include a number of "crowns" 98 at a proximal end thereof, which may correspond to the portions of the braided anchor member 70 where the wire(s) forming the braided anchor member 70 extends to a proximalmost extent. The crowns 98 may define a number of discrete locations where the plurality of filaments 90 engages and/or wraps over or around the braided anchor member 70. In some embodiments, the sheathing aid 200 may engage some of the crowns 98. In some embodiments, the sheathing aid 200 may engage all of the crowns 98. However, in some embodiments, the crowns 98 disposed radially adjacent to the locking elements 76 may not be engaged by sheathing aid 200, since the locking elements 76 are engaged by the plurality of fingers 58. The plurality of filaments 90 of the sheathing aid 200 may engage and/or wrap over or around the crowns 98 disposed between the locking elements 76.

Figure 14:
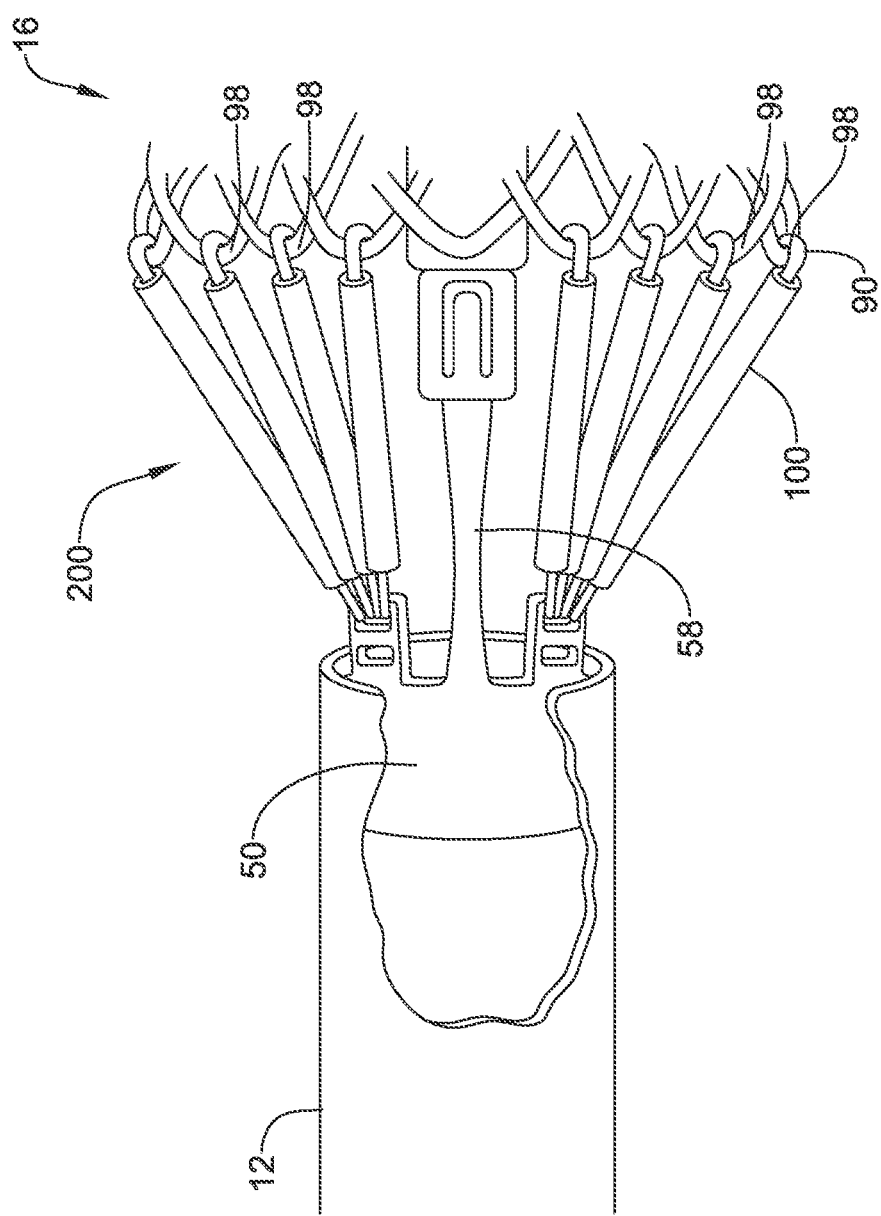
FIG. 14 illustrates selected components associated with an example medical device system in a deployed configuration prior to sheathing of an example medical implant.
Figure 15:
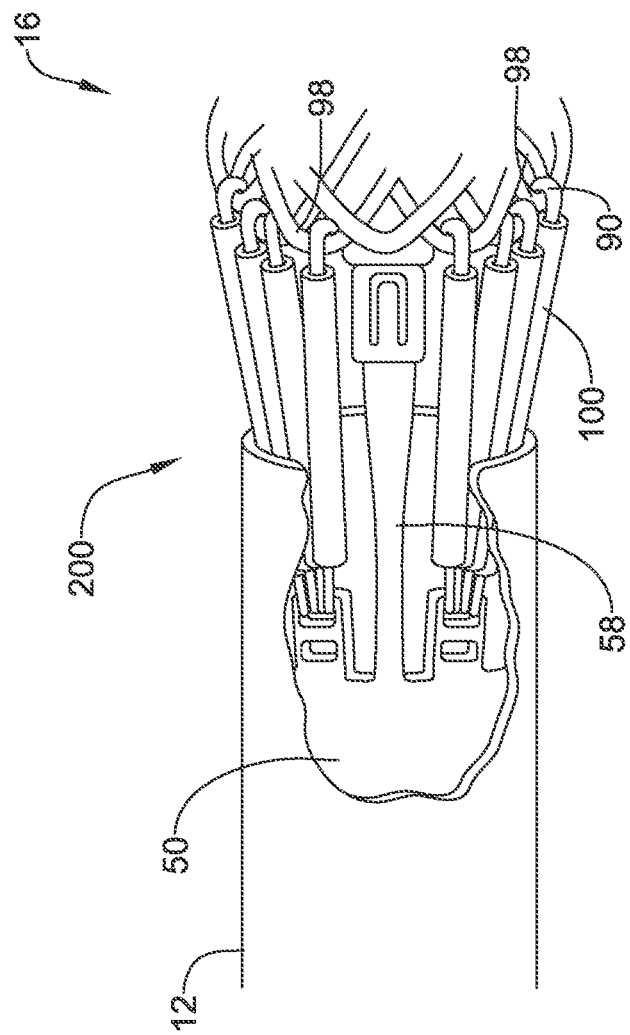
FIG. 15 illustrates selected components associated with an example medical device system in a partially-sheathed configuration during sheathing of an example medical implant.

FIGS. 14-15 illustrate an example sheathing aid 200 including a plurality of filaments 90 extending from the inner catheter 14 and/or the coupler ring 50 to a proximal end of the braided anchor member 70 and/or the medical implant 16. At least some of the plurality of filaments 90 of the sheathing aid 200 may include a tubular member 100 disposed thereon. In some embodiments, the at least some of the plurality of filaments 90 may comprise all of the plurality of filaments 90. In other words, each of the plurality of filaments 90 of the sheathing aid 200 may include a tubular member 100 disposed thereon. Each tubular member 100 may have a length, and in some embodiments, the length of all of the tubular members 100 may be substantially similar and/or the same. FIG. 14 illustrates a portion of the medical device system 10 in an "unsheathed" or "deployed" configuration. As the inner catheter 14 and/or the medical implant 16 is retracted, withdrawn, and/or translated proximally relative to the outer sheath 12 (and/or the outer sheath 12 is advanced distally relative to the inner catheter 14 and/or the medical implant 16), the plurality of filaments 90 and the tubular members 100 disposed thereon may contact a distal end of the outer sheath 12. In some embodiments, the plurality of filaments 90 and the tubular members 100 may act as levers against the distal end of the outer sheath 12 to provide a mechanical advantage for collapsing the braided anchor member 70 toward the "sheathed" or "delivery" configuration. FIG. 15 illustrates a portion of the medical device system 10 in a partially-sheathed configuration wherein the proximal end of the braided anchor member 70 and/or the medical implant 16 has been collapsed to a diameter similar to an inner diameter of the outer sheath 12.

Due to the attachment of the plurality of filaments 90 and/or the plurality of fingers 58 to each crown 98 of the braided anchor member 70, none of the crowns 98 may protrude radially outward to interfere with and/or catch or snag on the distal end of the outer sheath 12 during sheathing. Attaching the plurality of filaments 90 and/or the plurality of fingers 58 to each crown 98 of the braided anchor member 70 also distributes retraction and/or pulling forces among all of the crowns 98. Additionally, due to the use of a plurality of filaments 90 to attach to the crowns 98 and/or to serve as a sheathing aid 200, an overall outer profile of the braided anchor member 70 and/or the medical implant 16 may be reduced compared to a medical device system having a sheathing aid which is positioned along an outer surface of the braided anchor member 70, thereby reducing sheathing and unsheathing (e.g., deployment) forces and/or permitting a smaller diameter outer sheath 12 to be used, for example.

Figure 16:
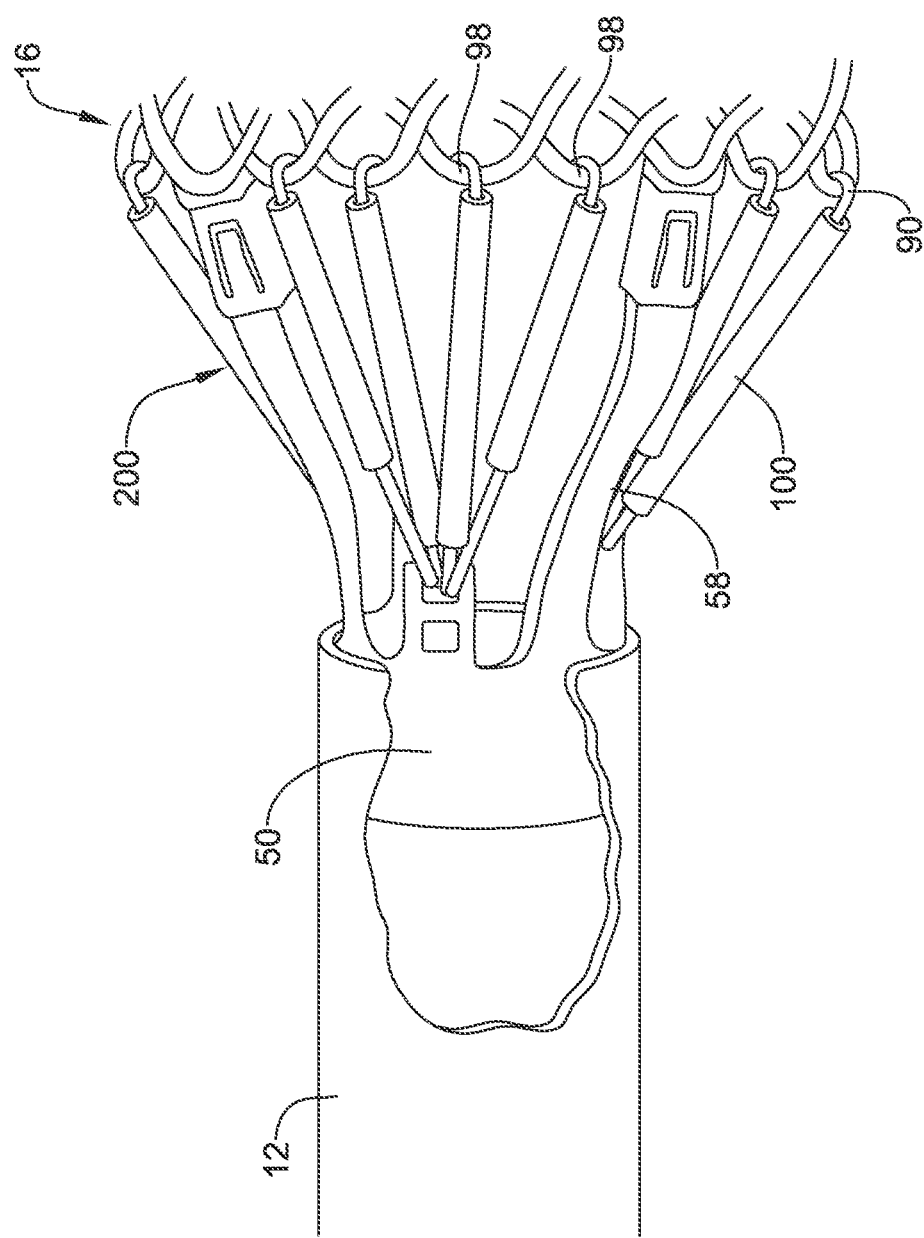
FIG. 16 illustrates selected components associated with an example medical device system in a deployed configuration prior to sheathing of an example medical implant.
Figure 17:
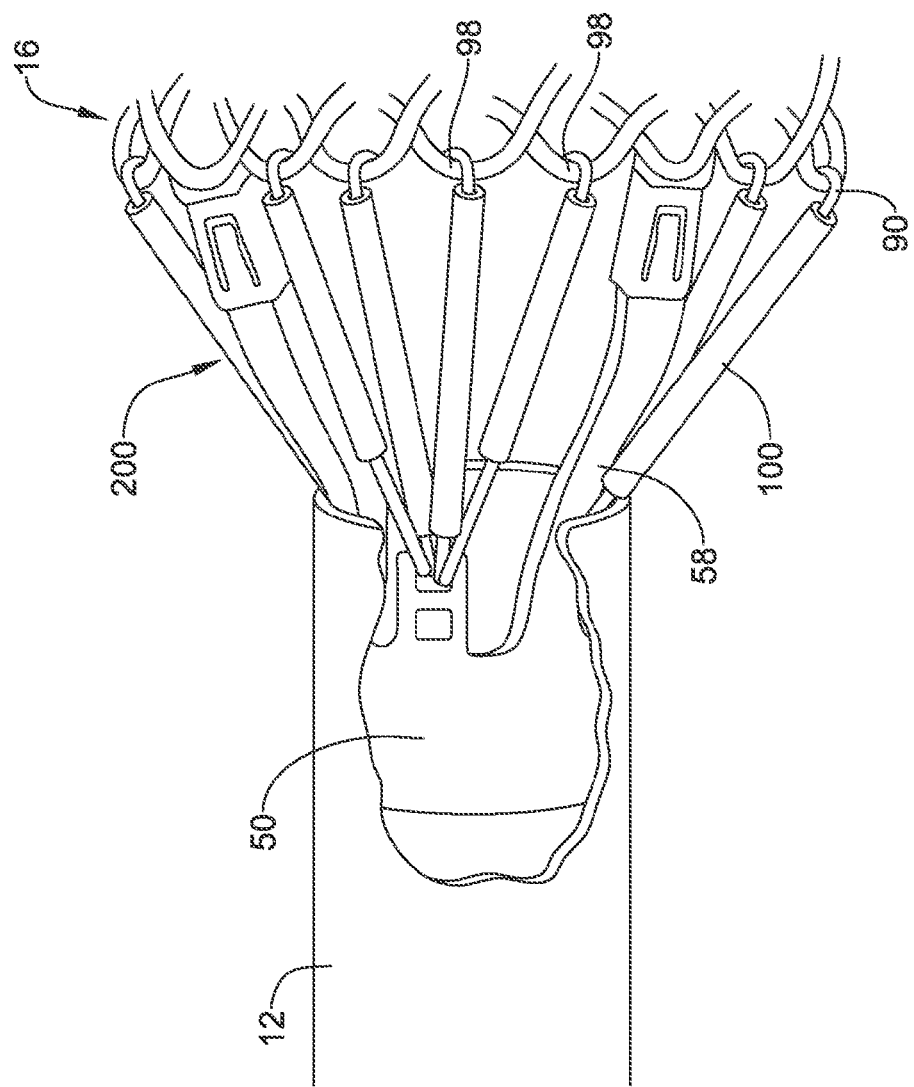
FIG. 17 illustrates selected components associated with an example medical device system in a partially-sheathed configuration during sheathing of an example medical implant.
Figure 20:
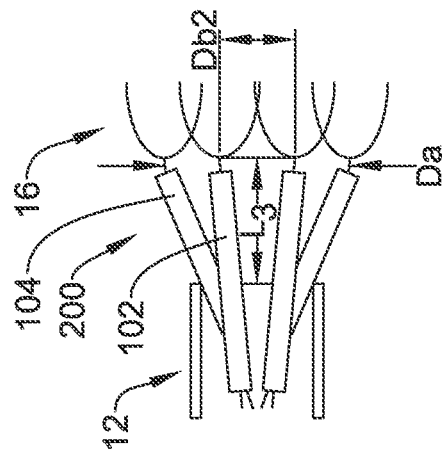
FIG. 20 illustrates selected components associated with an example medical device system at a second sheathing step of a partially-sheathed configuration during sheathing of an example medical implant.
Figure 19:
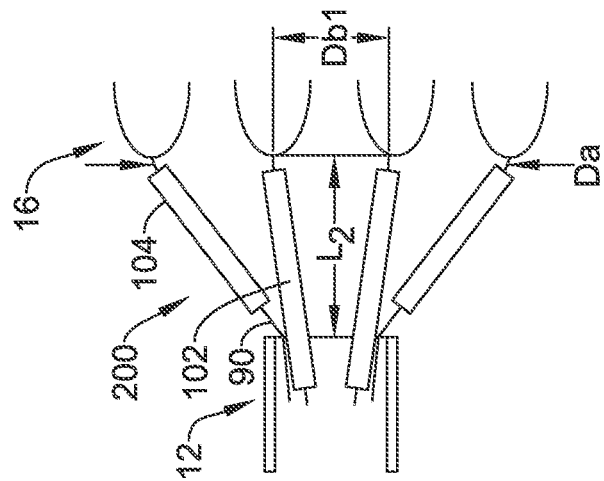
FIG. 19 illustrates selected components associated with an example medical device system at a first sheathing step of a partially-sheathed configuration prior during sheathing of an example medical implant.
Figure 18:
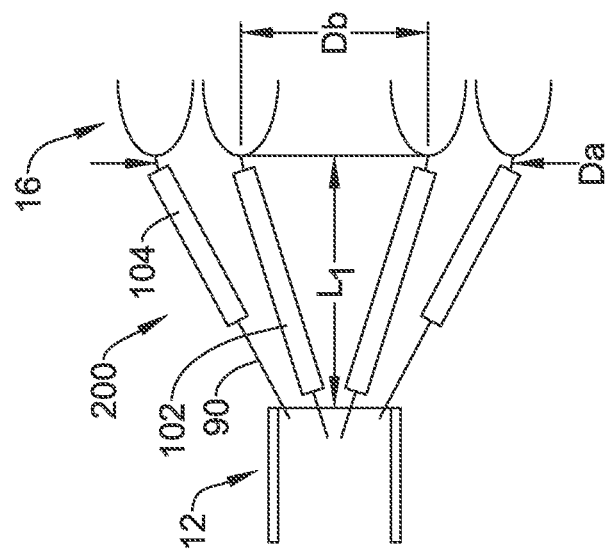
FIG. 18 illustrates selected components associated with an example medical device system in a deployed configuration prior to sheathing of an example medical implant.

FIGS. 16-20 illustrate an example sheathing aid 200 including a plurality of filaments 90 extending from the inner catheter 14 and/or the coupler ring 50 to a proximal end of the braided anchor member 70 and/or the medical implant 16. At least some of the plurality of filaments 90 of the sheathing aid 200 may include a tubular member 100 disposed thereon. In some embodiments, the at least some of the plurality of filaments 90 may comprise all of the plurality of filaments 90. In other words, each of the plurality of filaments 90 of the sheathing aid 200 may include a tubular member 100 disposed thereon. Each tubular member 100 may have a length, and in some embodiments, the length of the tubular members 100 may vary. FIGS. 16 and 18 illustrate a portion of the medical device system 10 in an "unsheathed" or "deployed" configuration. As the inner catheter 14 and/or the medical implant 16 is retracted, withdrawn, and/or translated proximally relative to the outer sheath 12 (and/or the outer sheath 12 is advanced distally relative to the inner catheter 14 and/or the medical implant 16), the plurality of filaments 90 and the tubular members 100 disposed thereon may contact a distal end of the outer sheath 12. In some embodiments, the plurality of filaments 90 and the tubular members 100 may act as levers against the distal end of the outer sheath 12 to provide a mechanical advantage for collapsing the braided anchor member 70 toward the "sheathed" or "delivery" configuration. FIGS. 17, 19, and 20 illustrate a portion of the medical device system 10 in partially-sheathed configurations wherein the proximal end of the braided anchor member 70 and/or the medical implant 16 has been partially collapsed toward an inner diameter of the outer sheath 12.

As may be seen, particular with respect to FIGS. 18-20, the varying lengths of the tubular members 100 may provide a sequential sheathing process wherein selected crowns 98 are collapsed radially inward at different times and/or positions in the sheathing process as the tubular members 100 come into contact with the distal end of the outer sheath 12. For example, in some embodiments, the tubular members 100 may include one or more first tubular members 102 having a first length and one or more second tubular members 104 having a second length shorter than the first length.

In some embodiments, at a first distance (L1) between the proximal end of the braided anchor member 70 and/or the medical implant 16 and the distal end of the outer sheath 12, the first tubular members may engage the distal end of the outer sheath 12. At the first distance (L1), the filaments 90 having the first tubular members 102 disposed thereon may form a first diameter (Db) and the filaments 90 having the second tubular members 104 disposed thereon may form a second diameter (Da), as seen in FIG. 18. At a second distance (L2) between the proximal end of the braided anchor member 70 and/or the medical implant 16 and the distal end of the outer sheath 12, the second distance (L2) being less than the first distance (L1), the filaments 90 having the first tubular members 102 disposed thereon may be reduced to a third diameter (Db1) less than the first diameter (Db) and the filaments 90 having the second tubular members 104 disposed thereon may maintain the second diameter (Da), as seen in FIG. 19. At a third distance (L3) between the proximal end of the braided anchor member 70 and/or the medical implant 16 and the distal end of the outer sheath 12, the third distance (L3) being less than the first distance (L1) and the second distance (L2), the filaments 90 having the first tubular members 102 disposed thereon may be even further reduced to a fourth diameter (Db2) less than the third diameter (Db1) and the filaments 90 having the second tubular members 104 disposed thereon may be reduced to a fifth diameter (Da1) less than the second diameter (Da), as seen in FIG. 20.

Due to the attachment of the plurality of filaments 90 and/or the plurality of fingers 58 to each crown 98 of the braided anchor member 70, none of the crowns 98 may protrude radially outward to interfere with and/or catch or snag on the distal end of the outer sheath 12 during sheathing. Attaching the plurality of filaments 90 and/or the plurality of fingers 58 to each crown 98 of the braided anchor member 70 also distributes retraction and/or pulling forces among all of the crowns 98. Additionally, due to the use of a plurality of filaments 90 to attach to the crowns 98 and/or to serve as a sheathing aid 200, an overall outer profile of the braided anchor member 70 and/or the medical implant 16 may be reduced compared to a medical device system having a sheathing aid which is positioned along an outer surface of the braided anchor member 70, thereby reducing sheathing and unsheathing (e.g., deployment) forces and/or permitting a smaller diameter outer sheath 12 to be used, for example.

Figure 21:
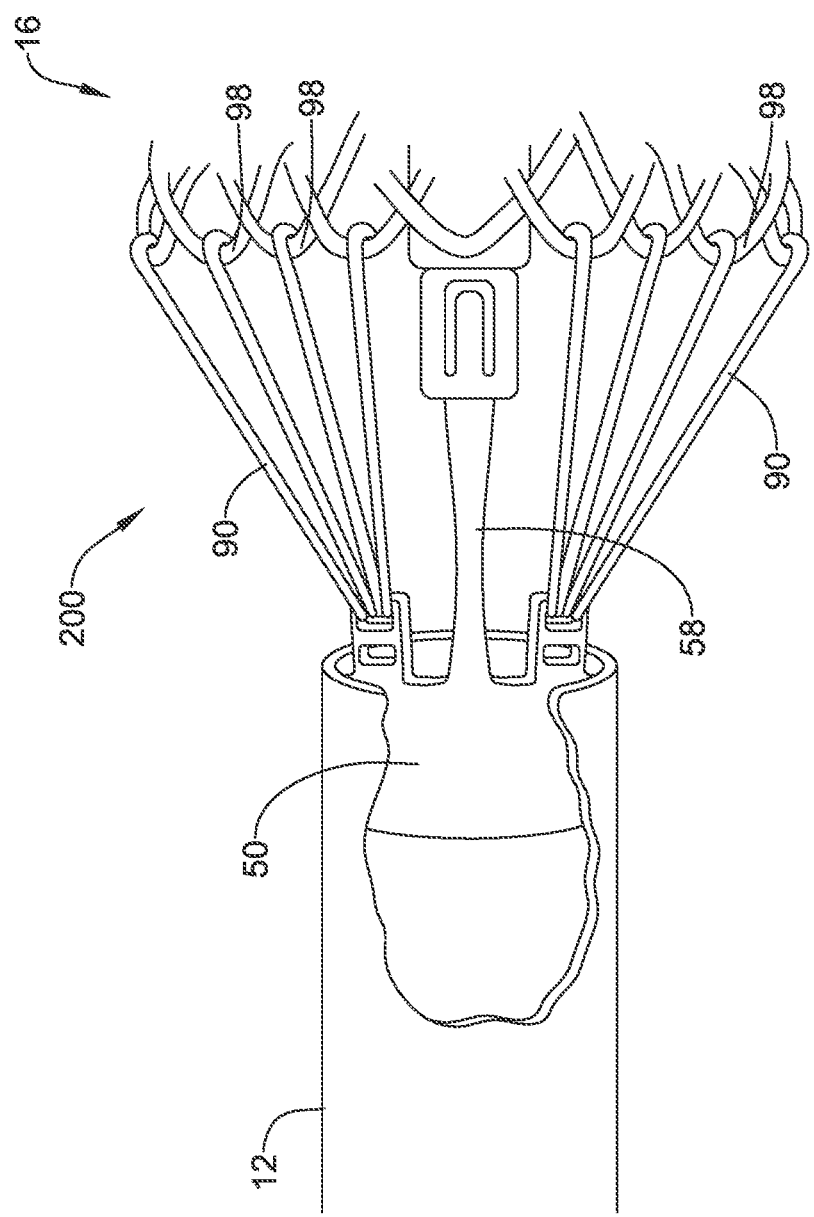
FIG. 21 illustrates selected components associated with an example medical device system in a deployed configuration prior to sheathing of an example medical implant.
Figure 22:
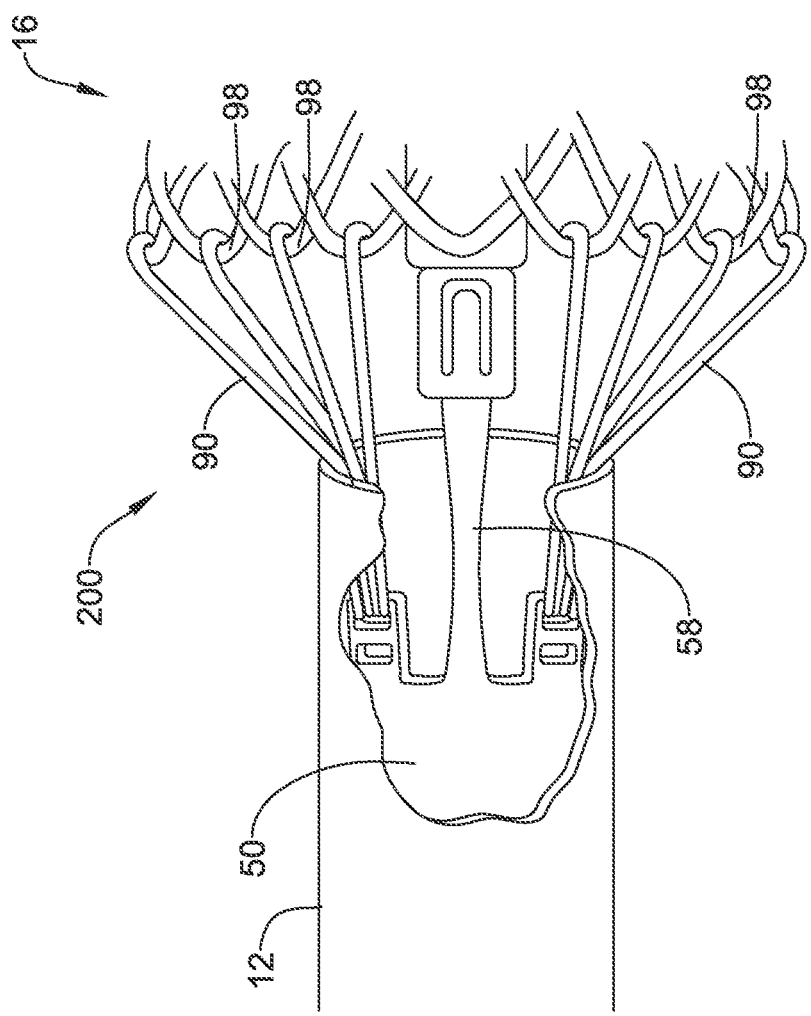
FIG. 22 illustrates selected components associated with an example medical device system in a partially-sheathed configuration during sheathing of an example medical implant.

FIGS. 21-22 illustrate an example sheathing aid 200 including a plurality of filaments 90 extending from the inner catheter 14 and/or the coupler ring 50 to a proximal end of the braided anchor member 70 and/or the medical implant 16. In contrast to the example sheathing aids shown in FIGS. 14-20, FIGS. 21-22 illustrate an example sheathing aid 200 lacking the tubular members 100 disposed on the plurality of filaments 90. FIG. 21 illustrates a portion of the medical device system 10 in an "unsheathed" or "deployed" configuration. As the inner catheter 14 and/or the medical implant 16 is retracted, withdrawn, and/or translated proximally relative to the outer sheath 12 (and/or the outer sheath 12 is advanced distally relative to the inner catheter 14 and/or the medical implant 16), the plurality of filaments 90 may contact a distal end of the outer sheath 12. In some embodiments, the plurality of filaments 90 may act as levers against the distal end of the outer sheath 12 for collapsing the braided anchor member 70 toward the "sheathed" or "delivery" configuration. FIG. 22 illustrates a portion of the medical device system 10 in a partially-sheathed configuration wherein the proximal end of the braided anchor member 70 and/or the medical implant 16 has not been collapsed due to pinching of the plurality of filaments 90. Such a configuration may result in increased sheathing forces compared to the configurations previously illustrated herein. However, due to the attachment of the plurality of filaments 90 and/or the plurality of fingers 58 to each crown 98 of the braided anchor member 70, retraction and/or pulling forces may be distributed among all of the crowns 98, and an overall outer profile of the braided anchor member 70 and/or the medical implant 16 may be reduced compared to a medical device system having a sheathing aid which is positioned along an outer surface of the braided anchor member 70, thereby permitting a smaller diameter outer sheath 12 to be used, for example.

The materials that can be used for the various components of the medical device system 10 (and/or other systems disclosed herein) and the various elements thereof disclosed herein may include those commonly associated with medical devices. For simplicity purposes, the following discussion makes reference to the delivery system and/or the medical implant 16. However, this is not intended to limit the devices and methods described herein, as the discussion may be applied to other elements, members, components, or devices disclosed herein, such as, but not limited to, the braided anchor member 70, the actuator element 84, the sheathing aid 200, the coupler assembly 78, the post member, the buckle member, etc. and/or elements or components thereof.

In some embodiments, the medical device system 10, the delivery system, the sheathing aid 200, and/or the medical implant 16, and/or components thereof, may be made from a metal, metal alloy, polymer (some examples of which are disclosed below), a metal-polymer composite, ceramics, combinations thereof, and the like, or other suitable material.

Some examples of suitable polymers may include polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane (for example, Polyurethane 85A), polypropylene (PP), polyvinylchloride (PVC), polyether-ester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), Marlex high-density polyethylene, Marlex low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro (propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS 50A), polycarbonates, ionomers, biocompatible polymers, other suitable materials, or mixtures, combinations, copolymers thereof, polymer/metal composites, and the like.

Some examples of suitable metals and metal alloys include stainless steel, such as 304V, 304L, and 316LV stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R30035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R30003 such as ELGILOY®, PHYNOX®, and the like); platinum enriched stainless steel; titanium; combinations thereof; and the like; or any other suitable material.

As alluded to herein, within the family of commercially available nickel-titanium or nitinol alloys, is a category designated "linear elastic" or "non-super-elastic" which, although may be similar in chemistry to conventional shape memory and super elastic varieties, may exhibit distinct and useful mechanical properties. Linear elastic and/or non-super-elastic nitinol may be distinguished from super elastic nitinol in that the linear elastic and/or non-super-elastic nitinol does not display a substantial "superelastic plateau" or "flag region" in its stress/strain curve like super elastic nitinol does. Instead, in the linear elastic and/or non-super-elastic nitinol, as recoverable strain increases, the stress continues to increase in a substantially linear, or a somewhat, but not necessarily entirely linear relationship until plastic deformation begins or at least in a relationship that is more linear than the super elastic plateau and/or flag region that may be seen with super elastic nitinol. Thus, for the purposes of this disclosure linear elastic and/or non-super-elastic nitinol may also be termed "substantially" linear elastic and/or non-super-elastic nitinol.

In some cases, linear elastic and/or non-super-elastic nitinol may also be distinguishable from super elastic nitinol in that linear elastic and/or non-super-elastic nitinol may accept up to about 2-5% strain while remaining substantially elastic (e.g., before plastically deforming) whereas super elastic nitinol may accept up to about 8% strain before plastically deforming. Both of these materials can be distinguished from other linear elastic materials such as stainless steel (that can also be distinguished based on its composition), which may accept only about 0.2 to 0.44 percent strain before plastically deforming.

In some embodiments, the linear elastic and/or non-super-elastic nickel-titanium alloy is an alloy that does not show any martensite/austenite phase changes that are detectable by differential scanning calorimetry (DSC) and dynamic metal thermal analysis (DMTA) analysis over a large temperature range. For example, in some embodiments, there may be no martensite/austenite phase changes detectable by DSC and DMTA analysis in the range of about −60 degrees Celsius (° C.) to about 120° C. in the linear elastic and/or non-super-elastic nickel-titanium alloy. The mechanical bending properties of such material may therefore be generally inert to the effect of temperature over this very broad range of temperature. In some embodiments, the mechanical bending properties of the linear elastic and/or non-super-elastic nickel-titanium alloy at ambient or room temperature are substantially the same as the mechanical properties at body temperature, for example, in that they do not display a super-elastic plateau and/or flag region. In other words, across a broad temperature range, the linear elastic and/or non-super-elastic nickel-titanium alloy maintains its linear elastic and/or non-super-elastic characteristics and/or properties.

In some embodiments, the linear elastic and/or non-super-elastic nickel-titanium alloy may be in the range of about 50 to about 60 weight percent nickel, with the remainder being essentially titanium. In some embodiments, the composition is in the range of about 54 to about 57 weight percent nickel. One example of a suitable nickel-titanium alloy is FHP-NT alloy commercially available from Furukawa Techno Material Co. of Kanagawa, Japan. Other suitable materials may include ULTANIUM™ (available from Neo-Metrics) and GUM METAL™ (available from Toyota). In some other embodiments, a superelastic alloy, for example a superelastic nitinol can be used to achieve desired properties.

In at least some embodiments, portions or all of the delivery system, the sheathing aid 200, and/or the medical implant 16, and/or components thereof, may also be doped with, made of, or otherwise include a radiopaque material. Radiopaque materials are understood to be materials capable of producing a relatively bright image on a fluoroscopy screen or another imaging technique during a medical procedure. This relatively bright image aids the user of the medical device system 10 in determining its location. Some examples of radiopaque materials can include, but are not limited to, gold, platinum, palladium, tantalum, tungsten alloy, polymer material loaded with a radiopaque filler, and the like. Additionally, other radiopaque marker bands and/or coils may also be incorporated into the design of the medical device system 10 to achieve the same result.

In some embodiments, a degree of Magnetic Resonance Imaging (MRI) compatibility is imparted into the medical device system 10. For example, the delivery system and/or the medical implant 16, and/or components or portions thereof, may be made of a material that does not substantially distort the image and create substantial artifacts (i.e., gaps in the image). Certain ferromagnetic materials, for example, may not be suitable because they may create artifacts in an MRI image. The delivery system and/or the medical implant 16, or portions thereof, may also be made from a material that the MRI machine can image. Some materials that exhibit these characteristics include, for example, tungsten, cobalt-chromium-molybdenum alloys (e.g., UNS: R30003 such as ELGILOY®, PHYNOX®, and the like), nickel-cobalt-chromium-molybdenum alloys (e.g., UNS: R30035 such as MP35-N® and the like), nitinol, and the like, and others.

In some embodiments, an exterior surface of the medical device system 10 (including, for example, an exterior surface of the delivery system) may be sandblasted, beadblasted, sodium bicarbonate-blasted, electropolished, etc. In these as well as in some other embodiments, a coating, for example a lubricious, a hydrophilic, a protective, or other type of coating may be applied over portions or all of the outer sheath, or in embodiments without an outer sheath over portions of the delivery system, or other portions of the medical device system 10. Hydrophobic coatings such as fluoropolymers provide a dry lubricity which improves device handling and device exchanges. Lubricious coatings improve steerability and improve lesion crossing capability. Suitable lubricious polymers are well known in the art and may include silicone and the like, hydrophilic polymers such as high-density polyethylene (HDPE), polytetrafluoroethylene (PTFE), polyarylene oxides, polyvinylpyrolidones, polyvinylalcohols, hydroxy alkyl cellulosics, algins, saccharides, caprolactones, and the like, and mixtures and combinations thereof. Hydrophilic polymers may be blended among themselves or with formulated amounts of water insoluble compounds (including some polymers) to yield coatings with suitable lubricity, bonding, and solubility.

The coating and/or sheath may be formed, for example, by coating, extrusion, co-extrusion, interrupted layer co-extrusion (ILC), or fusing several segments end-to-end. The layer may have a uniform stiffness or a gradual reduction in stiffness from the proximal end to the distal end thereof. The gradual reduction in stiffness may be continuous as by ILC or may be stepped as by fusing together separate extruded tubular segments. The outer layer may be impregnated with a radiopaque filler material to facilitate radiographic visualization. Those skilled in the art will recognize that these materials can vary widely without deviating from the scope of the present invention.

It should be understood that this disclosure is, in many respects, only illustrative. Changes may be made in details, particularly in matters of shape, size, and arrangement of steps without exceeding the scope of the invention. This may include, to the extent that it is appropriate, the use of any of the features of one example embodiment being used in other embodiments. The invention's scope is, of course, defined in the language in which the appended claims are expressed.

What is claimed is:

1. A medical device apparatus, comprising:
a medical implant including a braided anchor member operatively connected to a delivery system, the delivery system including a handle, an outer sheath extending distally from the handle, and an inner catheter disposed within the outer sheath; and
a sheathing aid connecting the delivery system to the medical implant, the sheathing aid being configured to guide the medical implant into the outer sheath upon compression of the sheathing aid as the sheathing aid is withdrawn into the outer sheath;
wherein the sheathing aid includes a plurality of filaments extending from the inner catheter to a proximal end of the braided anchor member, and a cleat disc disposed within a coupler ring fixedly attached to a distal end of the inner catheter;
wherein the plurality of filaments is releasably coupled to the cleat disc,
wherein the delivery system includes at least one actuator element extending from the inner catheter to the medical implant, the at least one actuator element being configured to reversibly shift the braided anchor member from an elongated delivery configuration to an enlarged deployed configuration,
wherein each of the at least one actuator element passes through the cleat disc.

2. The medical device apparatus of claim 1, wherein the cleat disc is movably disposed within the coupler ring.

3. The medical device apparatus of claim 1, wherein the cleat disc includes one or more cleat posts extending distally from the cleat disc.

4. The medical device apparatus of claim 3, wherein the plurality of filaments is releasably coupled to the one or more cleat posts.

5. The medical device apparatus of claim 3, wherein the one or more cleat posts comprises three cleat posts.

6. The medical device apparatus of claim 1, wherein the inner catheter includes a plurality of fingers extending distally from the coupler ring, the plurality of fingers being releasably coupled to the medical implant.

7. The medical device apparatus of claim 6, wherein the plurality of filaments extend through one or more openings disposed within a side wall of the coupler ring.

8. The medical device apparatus of claim 1, wherein at least some of the plurality of filaments each include a tubular member disposed thereon between the inner catheter and the medical implant.

9. The medical device apparatus of claim 8, wherein the at least some of the plurality of filaments comprises all of the plurality of filaments.

10. The medical device apparatus of claim 8, wherein each tubular member has a length, the length of all of the tubular members being substantially similar.

11. The medical device apparatus of claim 8, wherein the tubular members have varying lengths.

12. The medical device apparatus of claim 1, wherein each of the at least one actuator element includes a tubular sleeve disposed thereon and extending between the cleat disc and the medical implant.

13. The medical device apparatus of claim 1, wherein each of the at least one actuator element includes an enlarged portion disposed between the cleat disc and the medical implant.

14. The medical device apparatus of claim 1, wherein proximal translation of the at least one actuator element moves the cleat disc proximally after the braided anchor member has been shifted to the enlarged deployed configuration.

15. The medical device apparatus of claim 14, wherein moving the cleat disc proximally releases the plurality of filaments from the cleat disc.

16. The medical device apparatus of claim 1, wherein the braided anchor member includes a plurality of crowns, wherein each of the plurality of filaments is releasably attached at one of the plurality of crowns.

\* \* \* \* \*